United States Patent
Blackman et al.

(10) Patent No.: US 10,441,639 B2
(45) Date of Patent: Oct. 15, 2019

(54) PHARMACEUTICAL COMPOSITION COMPRISING PLASMINOGEN AND USES THEREOF

(71) Applicant: PROMETIC BIOTHERAPEUTICS, INC., Rockville, MD (US)

(72) Inventors: Davida Blackman, Gaithersburg, MD (US); Stacy Plum, Arlington, VA (US); William Garzon-Rodriguez, Exton, PA (US); Martin Robitaille, Saint-Columban (CA); Betty Yu, Frederick, MD (US)

(73) Assignee: PROMETIC BIOTHERAPEUTICS, INC., Rockville, MD (US)

( * ) Notice: Subject to any disclaimer, the term of this patent is extended or adjusted under 35 U.S.C. 154(b) by 0 days.

(21) Appl. No.: 15/536,877

(22) PCT Filed: Dec. 18, 2015

(86) PCT No.: PCT/CA2015/000606
§ 371 (c)(1),
(2) Date: Jun. 16, 2017

(87) PCT Pub. No.: WO2016/095013
PCT Pub. Date: Jun. 23, 2016

(65) Prior Publication Data
US 2017/0360902 A1 Dec. 21, 2017

Related U.S. Application Data

(60) Provisional application No. 62/094,556, filed on Dec. 19, 2014.

(51) Int. Cl.
| | | |
|---|---|---|
| A61K 38/48 | (2006.01) | |
| A61K 47/02 | (2006.01) | |
| A61K 47/10 | (2017.01) | |
| C12N 9/68 | (2006.01) | |
| A61K 9/00 | (2006.01) | |
| A61K 47/12 | (2006.01) | |
| A61K 47/18 | (2017.01) | |
| A61K 47/26 | (2006.01) | |
| A61K 9/19 | (2006.01) | |
| A61K 9/08 | (2006.01) | |

(52) U.S. Cl.
CPC .......... *A61K 38/484* (2013.01); *A61K 9/0019* (2013.01); *A61K 9/08* (2013.01); *A61K 9/19* (2013.01); *A61K 47/02* (2013.01); *A61K 47/10* (2013.01); *A61K 47/12* (2013.01); *A61K 47/183* (2013.01); *A61K 47/26* (2013.01); *C12N 9/6435* (2013.01); *C12Y 304/21007* (2013.01)

(58) Field of Classification Search
CPC .............. A61K 2300/00; A61K 31/525; A61K 31/198; A61K 31/375; A61K 31/385; A61K 9/0019; A61K 38/00; A61K 38/36; A61K 38/363; A61K 45/06; A61K 47/02; A61K 9/08; A61K 47/10; A61K 47/183; A61K 47/26; A61K 9/5153; A61K 31/16; A61K 31/185; A61K 31/721; A61K 38/02; A61K 38/484; A61K 38/4846; A61K 38/49; A61K 47/12; A61K 47/18; A61K 47/34; A61K 47/60; A61K 48/0041; A61K 9/1617; A61K 9/19; A61K 2035/124; A61K 31/713; A61K 38/26; A61K 38/482; A61K 41/0014; A61K 47/22; A61K 47/59; A61K 47/6937; A61K 48/00; A61K 49/225; A61K 9/0009; A61K 9/127; A61K 9/5146; A61K 9/7015
See application file for complete search history.

(56) References Cited

U.S. PATENT DOCUMENTS

| | | |
|---|---|---|
| 4,297,344 A | 10/1981 | Schwinn et al. |
| 5,290,764 A | 3/1994 | Duke, Jr. et al. |
| 2007/0134231 A1 | 6/2007 | Jani et al. |
| 2008/0008698 A1 | 1/2008 | Bartels et al. |

FOREIGN PATENT DOCUMENTS

| | | | | |
|---|---|---|---|---|
| CA | 1187411 A | | 5/1985 | |
| CA | 2796729 | * | 4/2011 | ............ A61K 47/26 |
| CA | 2796729 A1 | | 10/2011 | |
| EP | 0217379 A2 | | 4/1987 | |

(Continued)

OTHER PUBLICATIONS

Schott et al. "Therapy with a Purified Plasminogen Concentrate in an Infant with Ligneous Conjunctivitis and Homozygous Plasminogen Deficiency", The New England Journal of Medicine, vol. 339, No. 23, pp. 1679-1686, Dec. 3, 1998. (Year: 1998).*

(Continued)

*Primary Examiner* — Audrea B Coniglio
(74) *Attorney, Agent, or Firm* — Saliwanchik, LLoyd & Eisenschenk

(57) ABSTRACT

Pharmaceutical compositions comprising plasminogen or a biologically active variant thereof are disclosed. In an embodiment, the composition comprises a tonicity modifier, a bulking agent, and a stabilizing agent and has a pH of about 3.0 to about 10.0. In another embodiment, the composition contains an amount of particles in suspension equal to or greater than 10 μm which is lower than 6000 particles per 100 ml, and preferably lower than 2000 particles per 100 ml. Uses of these compositions as a medicament is contemplated. Various therapeutic uses of these pharmaceutical compositions is also contemplated.

38 Claims, 7 Drawing Sheets

(56) References Cited

FOREIGN PATENT DOCUMENTS

| JP | S62153224 A | 7/1987 |
|---|---|---|
| JP | 2005272403 A | 10/2005 |
| WO | 9415631 A1 | 7/1994 |

OTHER PUBLICATIONS

Darton ("Formulation for Improved Liquid Biotherapeutics", International Pharmaceutical Industry [Online], Summer/Autumn 2013, vol. 5, Issue 3. (Year: 2013).*
Darton, N., "Formulation for Improved Liquid Biotherapeutics." International Pharmaceutical Industry, 2013, 5 (3): 100-102.
Heidemann, D. G. et al., "Treatment of Ligneous Conjunctivitis with Topical Plasmin and Topical Plasminogen" Cornea, Nov. 2003, 22 (8): Abstract.
Schott, D. et al., "Therapy with a Purified Plasminogen Concentrate in an Infant with Ligneous Conjunctivitis and Homozygous Plasminogen Deficiency." The New England Journal of Medicine, Dec. 1998, 339(23): 1679-1686.
Watts, P. et al., "Effective treatment of ligneous conjunctivitis with topical plasminogen." American Journal of Ophtalmology, Apr. 2002, 133 (4): Abstract.

\* cited by examiner

Figure 1A

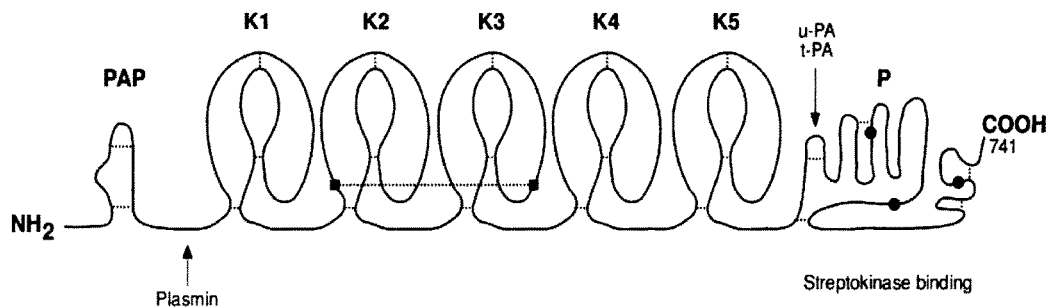

Figure 1B

Human plasminogen precursor (UniProt accession # P00747)

```
  1 mehkevvlll llflksgqge plddyvntqg aslfsvtkkq lgagsieeca akceedeeft
 61 crafqyhske qqcvimaenr kssiiirmrd vvlfekkvyl secktgngkn yrgtmsktkn
121 gitcqkwsst sphrprfspa thpsegleen ycrnpdndpq gpwcyttdpe krydycdile
181 ceeecmhcsg enydgkiskt msglecqawd sqsphahgyi pskfpnknlk knycrnpdre
241 lrpwcfttdp nkrwelcdip rcttpppssg ptyqclkgtg enyrgnvavt vsghtcqhws
301 aqtphthnrt penfpcknld enycrnpdgk rapwchttns qvrweyckip scdsspvste
361 qlaptappel tpvvqdcyhg dgqsyrgtss ttttgkkcqs wssmtphrhq ktpenypnag
421 ltmnycrnpd adkgpwcftt dpsvrweycn lkkcsgteas vvapppvvll pdvetpseed
481 cmfgngkgyr gkrattvtgt pcqdwaaqep hrhsiftpet npraglekny crnpdgdvgg
541 pwcyttnprk lydycdvpqc aapsfdcgkp qvepkkcpgr vvggcvahph swpwqvslrt
601 rfgmhfcggt lispewvlta ahcleksprp ssykvilgah qevnlephvq eievsrlfle
661 ptrkdiallk lsspavitdk vipaclpspn yvvadrtecf vtgwgetqgt fgagllkeaq
721 lpvienkvcn ryeflngrvq stelcaghla ggtdscqgds ggplvcfekd kyilqgvtsw
781 glgcarpnkp gvyvrvsrfv twiegvmrnn
```

Standards            Sample  0        1        2        3

Standards            Sample  0        1        2        3

PHARMACEUTICAL COMPOSITION COMPRISING PLASMINOGEN AND USES THEREOF

CROSS REFERENCE TO A RELATED APPLICATION

This application is a National Stage Application of International Application Number PCT/CA2015/000606, filed Dec. 18, 2015; which claims priority to U.S. Provisional Application No. 62/094,556, filed Dec. 19, 2014; both of which are incorporated herein by reference in their entirety.

FIELD OF INVENTION

The present invention relates to the field of medicine. More particularly, the invention relates to a pharmaceutical composition comprising plasminogen, and therapeutic uses thereof.

BACKGROUND OF INVENTION

Plasminogen is a zymogen of plasmin as shown in FIG. 1A. The amino acid sequence of the human plasminogen precursor is depicted in FIG. 1B. Human plasminogen contains 791 amino acids (precursor=810 amino acids) with a molecular weight of about 90 kDa and a pI of approximately 7.0, although differential glycosylation and/or removal of the N-terminal activation peptide can result in a pI range of 6.2 to 8.0. It is a single-chain protein with 24 intra-chain disulfide bridges, 5 kringle domains (involved in the binding to fibrin and to the inhibitor α2-antiplasmin), a serine protease domain (P), and an activation peptide (AP) consisting of the first 77 amino acids. There is one N-linked glycosylation site and one O-linked site, although a second O-linked site has been identified (Goldberg, 2006). Approximately 70% of the Plasminogen in circulation contains only O-linked glycosylation while the rest contains both N- and O-linked sugars.

Native Plasminogen is produced in two main forms, Glu-Plasminogen (Glu-Pg) and Lys-Plasminogen (Lys-Pg), named for the N-terminal amino acid of either glutamic acid or lysine. Glu-Pg is composed of the entire amino acid sequence designated by the gene sequence (excluding the activation peptide), while Lys-Pg is the result of a cleavage of the Glu-Pg between Lys-77 and Lys-78 (underlined in FIG. 1B). The circulating half-life of Lys-Pg is considerably shorter than Glu-Pg (2-2.5 days for Glu-Pg, 0.8 days for Lys-Pg). Glu-Pg is the dominant form of Pg present in plasma with very little Lys-Pg detected in the circulation (Violand, B. N., Byrne, R., Castellino F. J. (1978) The effect of α-,ω-Amino Acids on Human Plasminogen Structure and Activation. J Biol Chem. 253 (15): 5395-5401; Collen D, Ong E B, Johnson A J. (1975) Human Plasminogen: In Vitro and In Vivo Evidence for the Biological Integrity of $NH_2$- Terminal Glutamic Acid Plasminogen. Thrombosis Research. 7 (4):515-529).

Plasminogen is synthesized in the liver and secreted into plasma. Plasminogen is distributed throughout the body and when conditions are present for activation, the plasminogen pro-enzyme is converted to the active enzyme, plasmin, by tissue-type plasminogen activator (t-PA) or by urokinase plasminogen activator (u-PA). Plasmin then degrades fibrin and converts latent matrix metalloproteinases (pro-MMPs) into active MMPs, which in turn further degrade extracellular matrix (ECM) as part of the tissue healing/remodeling process. Plasminogen activation mediated by t-PA is primarily involved in fibrin homeostasis, while plasmin generation via u-PA, forming a complex with its receptor u-PAR, plays a role in tissue remodeling.

Plasmin is or was investigated for its potential use for the clearance of thrombotic occlusions in artificial devices and hemodialysis grafts, and for the treatment of posterior vitreous detachment (PVD) (U.S. Pat. No. 6,969,515; US 2010/0104551).

Plasminogen is investigated for its use in therapeutic indications such as wound healing, healing of a tympanic membrane perforation, healing of periodontal wound, infectious disease, oral health, diabetic ulcer, thrombolysis indications, such as coronary thrombosis, reperfusion injury to tissue, ischemia, infarction, brain edema, improvement of microcirculation, and modulation of complement pathway (U.S. Pat. Nos. 8,637,010; 8,679,482; 8,318,661; WO 95/12407; EP 0,631,786). As yet, no plasminogen is currently on the pharmaceutical market as a drug.

Historically, Lys-Pg was pharmaceutically commercialized for a period of time for hematologic purposes and has not been scientifically or medically used since 2000. A formulation of Lys-Pg is described in Schott et al., 1998, The New England Journal of Medicine, Vol. 339, No. 23, pp. 1679-1686). While available Lys-Pg was clinically used and investigated for the treatment of ligneous conjunctivitis, a clinical manifestation of the underlying condition hypoplasminogenimia (plasminogen deficiency type I). Hence systemic administration of Lys-Pg concentrates has been tested. Kraft et al. (Kraft J, Lieb W, Zeitler P, Schuster V. (2000) Ligneous conjunctivitis in a girl with severe type I plasminogen deficiency. Graefes Arch Clin Exp Ophthalmol. 238 (9):797-800) reported that daily infusion of Lys-Pg in a child with severe hypoplasminogenemia resulted in partial resolution of the conjunctival pseudo membranes. Schott et al. (1998) reported that, in a 6-month-old child, treatment with Lys-Pg preparation as a continuous infusion and later as daily bolus injections led to complete regression of the ligneous conjunctivitis within 4 weeks and normalized hyperviscous secretions in the respiratory tract as well as skin wound healing. Schuster et al (Schuster V, Hugle B, Tefs K (2007) Plasminogen deficiency. J Thromb Haemost 5(12):2315-2322) reported that plasminogen levels in patients with homozygous or compound heterozygous (the presence of two different mutant alleles at a particular gene locus, one on each chromosome of a pair) hypoplasminogenemia ranged from <1 to 9 mg/dL for plasminogen antigen plasma levels and <1% to 51% for functional plasminogen activity. It is important to note that the majority of these patients have some residual plasminogen activity levels. Thus, plasminogen replacement is expected to be effective, as it is an endogenous protein and is not expected to have immunogenicity or fibrinolytic activity concerns. Although systemic or topical plasminogen concentrates have been clearly documented as effective therapy leading to resolution and halts re-formation of the lesions (Watts P, Suresh P, Mezer E, Ells A, Albisetti M, Bajzar L, Marzinotto V, Andrew M, Massicotle P, Rootman D (2002) Effective treatment of ligneous conjunctivitis with topical plasminogen. Am J Ophthalmol 133(4):451-455, Heidemann D G, Williams G A, Hartzer M, Ohanian A, Citron M E (2003) Treatment of ligneous conjunctivitis with topical plasmin and topical plasminogen. Cornea 22(8):760-762; and Schott, 1998), no purified plasminogen product for topical or for systemic therapy is commercially available.

Only very recently, clinical trials were undertaken to utilize Glu-Pg for the treatment of the type I plasminogen deficiency (Clinical Trials.gov Identifier: NCT02312180)

and one of its clinical manifestation ligneous conjunctivitis utilizing a localized eye drop of Glu-Pg (ClinicalTrials.gov Identifier: NCT01554956).

Proteins may be stabilized either by changing their structural characteristics (internally) and/or by controlling the components in contact with them (externally). Some proteins have raised particular challenges with respect to handling and behaviour in pharmaceutical formulations due to their physico-chemical characteristics which often unfortunately leads to structural instability. They can actually undergo various types of degradations as exemplified by the following: 1) chemical processes leading to the formation of related impurities, which may involve hydrolysis, oxidation reactions, deamidation or structural rearrangements such as iso-asp or intramolecular truncations or 2) a physical process giving rise to aggregation/polymerization thus generating structural alterations which may impact on the biological activity and potentially enhance immunogenicity.

Formulation development generally refers to a process in which an active pharmaceutical ingredient (API) is characterized to a sufficient extent that it can be converted to a pharmaceutically acceptable drug substance. Biophysical characterization of drug substances must be performed to confirm that the correctly folded and biologically active structure is present. Several spectroscopic techniques (Fluorescence, CD, DSC, DLS, etc.) can be used to examine the tertiary structure of proteins in solution and to assess the stability and effect of different formulations conditions on protein structure. (Volkin, D. B. et al. "Preformulation studies as an essential guide to formulation development and manufacture of protein pharmaceutical." Development and manufacture of protein pharmaceuticals. Edited by Steve L. Nail and Michael J. Akers, Kluwer Academic 2002 Chapter 1, page 1-39; Cheng, W. et al. "Comparison of High-Throughput Biophysical Methods to Identify Stabilizing Excipients for a Model IgG2 Monoclonal Antibody: Conformational Stability and Kinetic Aggregation Measurements" Journal of Pharmaceutical Sciences, Vol. 101, No 5, page 1701-1720, 2012). In addition, often the pharmaceutical industry confirms the structural integrity of the API by performing a biologically assay for the release of the drug substance. Taken together they confirm that the preferred formulation has not inadvertently been modified by the formulation. Plasminogen is a protein that is mainly used in the preparation of plasmin for thrombolysis indications, such as coronary thrombosis, clearance of thrombotic occlusions in artificial devices and hemodialysis grafts, and for reperfusion injury to tissue, treating ischemia, infraction, brain edema, or for improving the microcirculation (WO 95/12407; U.S. Pat. No. 6,969,515; EP 0,631,786).

The administration of plasminogen has also been found useful in many therapeutic indications such as thrombolysis indications, such as coronary thrombosis, treating reperfusion injury to tissue, treating ischemia, infarction, brain edema, or for improving the microcirculation, wound healing, healing of a tympanic membrane perforation, healing of periodontal wound, infectious disease, oral health, diabetic ulcer, plasminogen-deficient subjects, and modulation of complement pathway (WO 95/12407; EP 0,631,786 U.S. Pat. No. 8,637,010; 8,679,482; 8,318,661).

There are several challenges encountered when formulating plasminogen. Some problems result from the plasmin contamination of the plasminogen formulation, which degrades plasminogen. Various approaches have been used for avoiding degradation of plasminogen including the addition of aprotinin, lysine, phenylmethanesulphonyl fluoride, soybean trypsin inhibitor or serine protease inhibitor (U.S. Pat. No. 4,177,262; 4,361,653, 5,304,383).

Other difficulties are represented by the turbidity or the presence of filamentous substances when plasminogen is solubilised in an aqueous solvent. To overcome this drawback, it has been proposed to combine plasminogen for example with a nonionic surfactant or with a mixture of sucrose, amino acid and albumin (WO 94/15631).

There is no known commercial formulation of Glu-Pg for human therapeutic use. The only formulations of Glu-Pg that are known are for research only.

There is a need for the development of a pharmaceutical composition of plasminogen.

The present description refers to a number of documents, the content of which is herein incorporated by reference in their entirety.

BRIEF SUMMARY OF THE INVENTION

The present invention relates to a pharmaceutical composition comprising plasminogen, and uses thereof.

The present invention relates to the following items 1 to 61:

1. A pharmaceutical composition comprising:
plasminogen, or a biologically active variant thereof;
a tonicity modifier; and
a stabilising agent;
wherein the composition has a pH of about 3.0 to about 10.0.

2. The pharmaceutical composition of item 1, wherein the pH is from 5.0 to 8.0; or from 6.0 to 8.0; or from 6.5 to 7.5.

3. The pharmaceutical composition of item 1, wherein the concentration of the plasminogen or biologically active variant thereof is about 0.01 mg/ml to about 80 mg/ml, or from about 5 mg/ml to about 60 mg/ml.

4. The pharmaceutical composition of item 3, wherein the concentration of the plasminogen or biologically active variant thereof is about 40, 30, 20, 10 or 5 mg/ml.

5. The pharmaceutical composition of any one of items 1 to 4, wherein the plasminogen or biologically active variant thereof represents at least 80% of the total protein content of the composition or more than 90% of the total protein content of the composition.

6. The pharmaceutical composition of item 5, wherein the plasminogen or biologically active variant thereof represents more than 95 or 98% of the total protein content of the composition.

7. The pharmaceutical composition of any one of items 1 to 6, wherein the stabilising agent comprises (i) an amino acid, (ii) an amino acid salt, (ii) an amino acid analog, or (iv) any mixture of (i), (ii) and/or (iii).

8. The pharmaceutical composition of item 7, wherein the amino acid, amino acid salt or amino acid analog is arginine, proline, glutamic acid, aspartic acid, glycine, alanine, cysteine, lysine, a lysine analog or epsilon-amino caproic acid.

9. The pharmaceutical composition of item 8, wherein the stabilising agent is arginine.

10. The pharmaceutical composition of any one of items 1 to 9, wherein the stabilising agent is in a concentration of about 20 mM to about 200 mM.

11. The pharmaceutical composition of item 10, wherein the stabilising agent is in a concentration of about 25 mM to about 75 mM.

12. The pharmaceutical composition of any one of items 1 to 11, wherein the tonicity modifier is sodium chloride, calcium chloride, magnesium chloride, sucrose, trehalose, sorbitol, mannitol, glycerol, lactose, sorbitol, dextrose, cyclodextrin, raffinose, polyethylene glycol, hydroxyethyl starch, glycine glutamic acid, alanine, dextran, PVP (poly vinyl pyrrolidone), or any combination thereof.

13. The pharmaceutical composition of item 12, wherein the tonicity modifier is sodium chloride.

14. The pharmaceutical composition of any one of items 1 to 13, wherein the tonicity modifier is present in a concentration of about 30 mM to about 250 mM.

15. The pharmaceutical composition of item 14, wherein the tonicity modifier is present in a concentration of between about 25 mM to about 50 mM, or of about 35 mM.

16. The pharmaceutical composition of any one of items 1 to 15, further comprising a bulking agent.

17. The pharmaceutical composition of item 16, wherein the bulking agent is glycine, glutamic acid, alanine, mannitol, sorbitol, hydroxyethyl starch, dextran, PVP (poly vinyl pyrrolidone), mannitol, polyethylene glycol, sorbitol, maltitol, lactitol, maltotriitol, xylitol or any combination thereof.

18. The pharmaceutical composition of item 17, wherein the bulking agent is mannitol or sorbitol.

19. The pharmaceutical composition of any one of items 16 to 18, wherein the bulking agent is in a concentration of about 50 mM to about 300 mM.

20. The pharmaceutical composition of item 19, wherein the bulking agent is in a concentration of about 50 to about 125 mM.

21. The pharmaceutical composition of any one of items 1 to 20, further comprising a reducing sugar.

22. The pharmaceutical composition of item 21, wherein the reducing sugar is fructose, mannose, maltose, lactose, arabinose, xylose, ribose, rhamnose, galactose, glucose, sucrose or any combination thereof.

23. The pharmaceutical composition of any one of items 1 to 22, further comprising a non-reducing sugar.

24. The pharmaceutical composition of item 23, wherein the non-reducing sugar is sucrose, trehalose, sorbose, melezitose, raffinose, or any combination thereof.

25. The pharmaceutical composition of any one of items 1 to 24, wherein the pharmaceutical composition has an osmolality between about 180 mOsm and about 350 mOsm.

26. The pharmaceutical composition of any one of items 1 to 25, further comprising a preservative.

27. The pharmaceutical composition of item 26, wherein the preservative is m-cresol, benzyl alcohol, methanol, ethanol, iso-propanol, butyl paraben, ethyl paraben, methyl paraben, phenol, glycerol, xylitol, resorcinol, catechol, 2,6-dimethylcyclohexanol, 2-methyl-2,4-pentadiol, dextran, polyvinylpyrrolidone, 2-chlorophenol, benzethonium chloride, merthiolate (thimersosal), benzoic acid (propyl paraben) MW 180.2, benzoic acid MW 122.12, benzalkonium chloride, chlorobutanol, sodium benzoate, sodium propionate, cetylpyridinium chloride, or any combination thereof.

28. The pharmaceutical composition of item 26 or 27, wherein the concentration of the preservative is from about 0.005 to about 10% (w/v).

29. The pharmaceutical composition of any one of items 1 to 28, wherein said plasminogen or a biologically active variant thereof is human plasminogen.

30. The pharmaceutical composition of any one of items 1 to 29, wherein said plasminogen or a biologically active variant thereof is constituted of more than about 80% of Glu-plasminogen.

31. The pharmaceutical composition of any one of items 1 to 29, wherein said plasminogen or a biologically active variant thereof is Glu-plasminogen.

32. The pharmaceutical composition of any one of items 1 to 31, wherein the composition contains an amount of particles equal to or greater than 10 µm which is lower than 6000 particles per 100 ml.

33. The pharmaceutical composition of item 32, wherein the amount of particles is lower than 2000 or 1000 particles per 100 ml.

34. The pharmaceutical composition of any one of items 1 to 33, which is suitable for intravenous, subcutaneous, topical, intradermal, ophthalmic and/or intramuscular administration.

35. The pharmaceutical composition of any one of items 1 to 34, which is a liquid composition, a liquid composition suitable for lyophilisation, a liquid composition suitable for freezing, a lyophilised composition, a frozen composition or a reconstituted composition.

36. The pharmaceutical composition of any one of items 1 to 34, which is a liquid, a gel, a cream, or an ointment.

37. The pharmaceutical composition of any one of items 1 to 36, for use as a medicament.

38. A pharmaceutical composition comprising plasminogen or a biologically active variant thereof, which contains an amount of particles equal to or greater than 10 µm which is lower than 6000 particles per 100 ml.

39. The pharmaceutical composition of item 38, wherein the amount of particles is lower than 2000 or 1000 particles per 100 ml.

40. The pharmaceutical composition of item 38 or 39, which further comprises a stabilising agent.

41. The pharmaceutical composition of item 40, wherein the stabilising agent comprises (i) an amino acid, (ii) an amino acid salt, (ii) an amino acid analog, or (iv) any mixture of (i), (ii) and/or (iii).

42. The pharmaceutical composition of item 41, wherein the amino acid, amino acid salt or amino acid analog is arginine, proline, glutamic acid, aspartic acid, glycine, alanine, cysteine, lysine, a lysine analog or epsilon-amino caproic acid.

43. The pharmaceutical composition of item 42, wherein the stabilising agent is arginine.

44. The pharmaceutical composition of any one of items 40 to 43, wherein the stabilising agent is in a concentration of about 25 mM to about 75 mM.

45. The pharmaceutical composition of any one of items 38 to 44, wherein the concentration of the plasminogen or biologically active variant thereof is from about 0.01 mg/ml to about 80 mg/ml.

46. The pharmaceutical composition of item 45, wherein the concentration of the plasminogen or biologically active variant thereof is from about 5 mg/ml to about 60 mg/ml.

47. The pharmaceutical composition of any one of items 38 to 46, wherein the plasminogen or biologically active variant thereof represents more than about 95% of the total protein content of the composition, or more than about 98% of the total protein content of the composition 48. The pharmaceutical composition of any one of items 38 to 47, which further comprises a tonicity modifier.

49. The pharmaceutical composition of item 48, wherein the tonicity modifier is sodium chloride, calcium chloride, magnesium chloride, sucrose, trehalose, sorbitol, mannitol, glycerol, lactose, sorbitol, dextrose, raffinose, polyethylene glycol, hydroxyethyl starch, glycine glutamic acid, alanine, dextran, PVP (poly vinyl pyrrolidone), or any combination thereof.

50. The pharmaceutical composition of item 49, wherein the tonicity modifier is sodium chloride.

51. The pharmaceutical composition of item 48, 49 or 50, wherein the tonicity modifier is present in a concentration of about 30 mM to about 250 mM.

52. The pharmaceutical composition of any one of items 38 to 51, which further comprises a bulking agent.

53. The pharmaceutical composition of item 52, wherein the bulking agent is glycine, glutamic acid, alanine, mannitol, sorbitol, hydroxyethyl starch, dextran, PVP (poly vinyl pyrrolidone), mannitol, polyethylene glycol, sorbitol, maltitol, lactitol, maltotriitol, xylitol or any combination thereof.

54. The pharmaceutical composition of item 53, wherein the bulking agent is mannitol or sorbitol.

55. The pharmaceutical composition of item 52, 53 or 54, wherein the bulking agent is in a concentration of about 50 mM to about 300 mM.

56. The pharmaceutical composition of any one of items 38 to 55, wherein the pharmaceutical composition has an osmolality between about 180 mOsm and about 350 mOsm.

57. The pharmaceutical composition of any one of items 38 to 61, wherein the pharmaceutical composition has a pH of about 6.5 to about 8.0.

58. The pharmaceutical composition of any one of items 38 to 57, wherein said plasminogen or a biologically active variant thereof is human plasminogen.

59. The pharmaceutical composition of any one of items 38 to 58, wherein said plasminogen or a biologically active variant thereof consists of more than 80% of Glu-plasminogen.

60. The pharmaceutical composition of any one of items 38 to 58, wherein said plasminogen or a biologically active variant thereof is Glu-plasminogen.

61. The pharmaceutical composition of any one of items 38 to 60, for use as a medicament.

Further aspects of the invention will be apparent to a person skilled in the art from the following description, claims, and generalizations herein.

BRIEF DESCRIPTION OF THE FIGURES

FIG. 1A is a schematic of the primary structure of plasminogen showing its kringle domains, plasmin cleavage site and streptokinase binding site.

FIG. 1B shows the amino acid sequence of human plasminogen precursor. The sequence of the mature form is in bold, and the two lysine residues between which there is a cleavage to generate Lys-Pg are underlined.

DETAILED DESCRIPTION OF THE INVENTION

Figure 2:
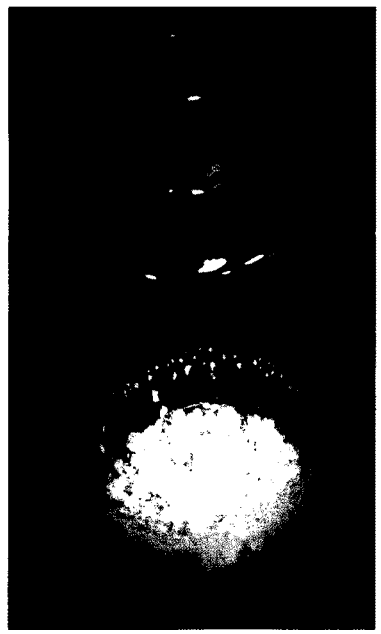
FIG. 2 is a picture of a vial containing the placebo (without Pg) of Formulation 1 after lyophilisation.
Figure 3:
FIG. 3 is a picture a vial containing Formulation 1 (described in Table 1A) after lyophilisation.
Figure 4:
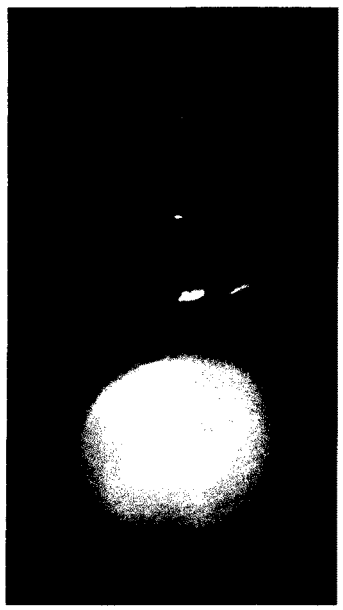
FIG. 4 is a picture a vial containing the placebo (without Pg) of Formulation 2 after lyophilisation.
Figure 5:
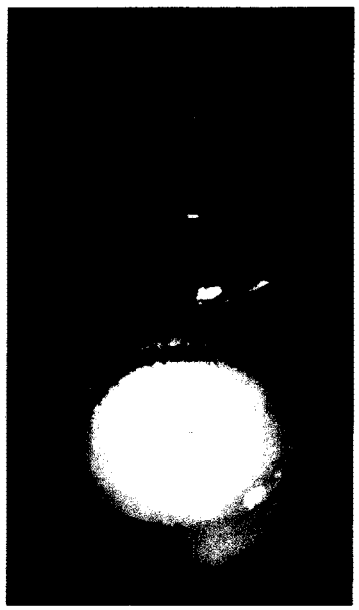
FIG. 5 is a picture a vial containing Formulation 2 (described in Table 1A) after lyophilisation.
Figure 6:
FIG. 6 is a picture a vial containing the placebo (without Pg) of Formulation 3 after lyophilisation.
Figure 7:
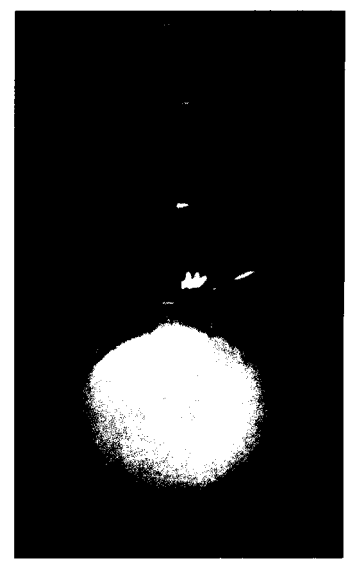
FIG. 7 is a picture a vial containing Formulation 3 (described in Table 1A) after lyophilisation.
Figure 8:
FIG. 8 is a picture a vial containing the placebo (without Pg) of Formulation 4 after lyophilisation.
Figure 9:
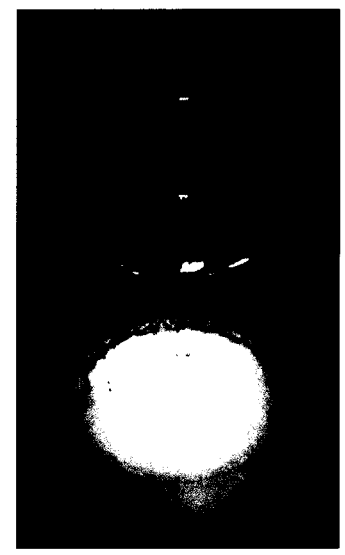
FIG. 9 is a picture a vial containing Formulation 4 (described in Table 1A) after lyophilisation.
Figure 10:
FIG. 10 is a picture a vial containing the placebo (without Pg) of Formulation 5 after lyophilisation.
Figure 11:
FIG. 11 is a picture a vial containing Formulation 5 (described in Table 1A) after lyophilisation.

Disclosed herein is a pharmaceutical composition comprising plasminogen, or a biologically active variant thereof.

Also disclosed herein is a pharmaceutical composition comprising:
plasminogen, or a biologically active variant thereof;
a tonicity modifier; and
a stabilising agent;
the composition having a pH of about 3.0 to about 10.0; preferably of about 5.0 to about 8.0; more preferably of about 6.0 to about 8.0; and further preferably of about 6.5 to about 7.5.

The present invention concerns a pharmaceutical composition comprising plasminogen or a biologically active variant thereof, with an increased robustness. The present invention concerns a pharmaceutical composition comprising plasminogen or a biologically active variant thereof, that has count of particles of 10 μm or greater that is lower than 6000 particles per 100 mL of composition, or lower than 5000 particles per 100 mL of composition, or lower than 4000 particles per 100 mL of composition, or lower than 3000 particles per 100 mL of composition, or lower than 2000 particles per 100 mL of composition or lower than 1000 particles per 100 mL of composition. In an embodiment of the present invention, the count of particles remains low after lyophilisation and reconstitution. In an embodiment of the present invention, repeated preparations of the same composition provide no variation of the count of particles.

The term "Plasminogen" as used herein refers to any form of a native plasminogen polypeptide (e.g., Glu-plasminogen or Lys-plasminogen) from any animal, for example a mammal (e.g., human). Plasminogen is a pro-enzyme is converted to the active enzyme, plasmin, by tissue-type plasminogen activator (t-PA) or by urokinase plasminogen activator (u-PA). Plasmin then degrades fibrin and converts latent matrix metalloproteinases (pro-MMPs) into active MMPs, which in turn further degrade extracellular matrix (ECM) as part of the tissue healing/remodeling process. The term "biologically active variant" as used herein refers to a mutated plasminogen polypeptide that retains the biological activity of native plasminogen, i.e. the ability to be converted to a plasmin polypeptide (by t-PA and or u-PA) that is able to degrade fibrin and converts latent matrix metalloproteinases (pro-MMPs) into active MMPs. The variant may comprises one or more amino acid substitutions, deletions/truncations (N-terminal, C-terminal, and/or internal amino acid deletions/truncations), additions (N-terminal, C-terminal, and/or internal amino acid additions). The biologically active variants may exhibit a biological activity (e.g., enzymatic activity of the resulting plasmin) that is lower, higher or similar to that of a native plasminogen polypeptide. In embodiments, the variant has at least 60, 70, 75, 80, 85, 90, or 95% amino acid sequence identity with a native plasminogen polypeptide. Biologically active plasminogen variants are described, for example, in WO2012/093132, WO2013/024074 and in Wang et al. (1995, Protein Science 4, 1758-1767), and included the truncated variants of plasminogen commonly referred to as "midiplasminogen", "miniplasminogen", "microplasminogen" and "delta-plasminogen" that lack one or more kringle domains and/or parts thereof. In an embodiment, the plasminogen is human plasminogen. In a further embodiment, the composition comprises native human plasminogen. The plasminogen may be obtained from several sources. It may be obtained by recombinant synthesis, or extracted/purified from blood, plasma or a blood-derived solution. Plasminogen can be extracted from blood or plasma by Cohn fractionation or by precipitation. Plasminogen can be purified from plasma or blood-derived solution by a binding affinity chromatography, such as the method described in WO 2006/120423, or produced recombinantly.

In an embodiment, the plasminogen or biologically active variant thereof is present in a concentration of about 0.01 mg/ml to about 80 mg/ml; preferably about 1 mg/ml to about 60 mg/ml; preferably about 5 mg/ml to about 60 mg/ml; preferably about 5 mg/ml to about 40 mg/ml; preferably of about 2 mg/ml to about 30 mg/ml, more preferably of about 2 mg/ml to about 20 mg/ml, and further preferably of about 80, 70, 60, 50, 40, 30, 25, 20, 15, 14, 13, 12, 11, 10, 9, 8, 7, 6, 5, 4, 3, 2, 1, 0.5, 0.1, 0.05 or 0.01 mg/ml.

In an embodiment of the present invention, the plasminogen or biologically active variant thereof contained in the pharmaceutical composition has a purity of more than about 80%, or more than about 90%, or more than about 95%, or more than about 98%. The term "about" refers a variation of value by more or less 10%.

The pH of the present composition can be from about 3.0 to about 10.0; from about 5.0 to about 8.0; from about 6.0 to about 8.0; or from about 6.5 to about 7.5. In embodiments, the pH of the present composition is about 3.0, 3.5, 4.0, 4.5, 5.0, 5.5, 6.0, 6.1, 6.2, 6.3, 6.4, 6.5, 6.6, 6.7, 6.8, 6.9, 7.0, 7.1, 7.2, 7.3, 7.4, 7.5, 8.0, 8.5, 9.0 or 10.0. To maintain the composition at such a pH, the present composition preferably comprises a buffer. Many buffers can be used within the scope of the present invention, including the following buffers depending on the desired pH:

| Buffer | Desired pH |
|---|---|
| Citrate/phosphate | 3.0, 3.5, 4.0, 4.5, 5.0, 5.5, 6.0, 6.5 to 7.0, 7.5, 8.0, and any pH from 2.0 and 8.0 |
| Citrate | 3.0 to 6.5 |
| Acetate | any pH from 3.6 to 5.6, for example 4.0, 4.5, 5.0, or 5.5 |
| Sodium acetate | 3.6 to 5.6 |
| Formate | 3.0 to 4.5 |
| Sodium formate | any pH from 5.0 and 6.0, for example 5.0, 5.5, or 6.0 |
| Malate | 4.0 to 6.0 |
| Phosphate | any pH from 6.5 and 8.0, for example 6.5, 7.0, 7.5, or 8.0 |
| PBS, TBS, TNT, PBT | 7.0 to 7.5 |
| Sorensen's | 5.8 to 8.0 |
| Succinate | any pH from 5.5 to 6.5, for example 6.0 |
| Carbonate | any pH from 6.0 to 8.0, for example 6.5 |
| Histidine | any pH from 5.0 and 7.0, for example 5.0, 5.5, 6.0, or 6.5 to 7.0 |
| Borate | 9 to 10 |
| Glycine-NaOH | 8.6 to 10 |
| Succinate | 5.5 to 6.5 |
| Maleate | 5.5 to 7.2 |
| Tris | 7.2 to 9.0 |
| BIS-Tris | any pH from 5.8 and 7.2 |
| PIPES | any pH from 6.1 and 7.5 |
| MOPS | any pH from 6.2 and 7.6 |
| HEPES | any pH from 6.8 and 8.2 |
| MES | any pH from 5.5 and 6.7 |
| ACES | any pH from 6.1 and 7.5 |

In an embodiment, the buffer comprises a combination of two buffers; such as Citrate/Phosphate, Citrate/Histidine, Acetate/Histidine or Succinate/Histidine. In an embodiment of the present invention, the buffer does not comprise a citrate buffer. In another embodiment, the buffer is citrate, phosphate ($K_2HPO_4/NaHPO_4$), histidine, or succinate. In another embodiment, the buffer is phosphate ($K_2HPO_4/NaHPO_4$), histidine, or succinate.

In an embodiment, the concentration of the buffer is from about 10 mM to about 50 mM, or from about 10 mM to about 30 mM, for example about 2 mM or about 10 mM.

As used herein, a "tonicity modifier" refers to a compound which is used to adjust the tonicity of the pharmaceutical composition. In an embodiment, the tonicity modifier is present in an amount that renders the composition isotonic. In another embodiment, the tonicity modifier is present in an amount that renders the composition hypertonic or hypotonic. In an embodiment, the tonicity modifier is sodium chloride, calcium chloride, magnesium chloride, potassium chloride, $Na_2SO_4$, $ZnCl_2$, borate, pharmaceutically acceptable monovalent salt, pharmaceutically acceptable divalent salt, pharmaceutically acceptable trivalent salt, pharmaceutically acceptable quatravalent salt, sucrose, trehalose, sorbitol, mannitol, glycerol, lactase, sorbitol, dextrose, cyclodextrin, raffinose, a sugar alcohol, polyethylene glycol, hydroxyethyl starch, glycine glutamic acid, alanine, dextran PVP (poly vinyl pyrrolidone), or any combination thereof. "Isotonic" is meant that the composition of the present invention has essentially the same osmolality than the osmolality of human blood. Isotonic compositions generally have an osmolality from about 250 to about 330 mOsm. Osmolarity can be measured using a vapor pressure or ice-freezing type osmometer, for example. In an embodiment, the pharmaceutical composition comprises a mixture of two tonicity modifiers. In another embodiment, the pharmaceutical composition comprises a mixture of three tonicity modifiers. In an embodiment, the tonicity modifier is a sugar or comprises a sugar, or a mixture of sugars. In an embodiment, the tonicity modifier is sodium chloride. In an embodiment, the concentration of the tonicity modifier concentration is from about 30 mM to about 250 mM, or from about 20 mM to about 150 mM, or from about 30 mM to about 100 mM. In an embodiment, the concentration of the tonicity modifier concentration is about 34 mM, or about 35 mM, or about 68 mM, or about 75 mM. In an embodiment, the concentration of the tonicity modifier is adjusted so that the resulting osmolality of the composition falls within the desired range.

In an embodiment, the composition further comprises a bulking agent. As used herein, a "bulking agent" refers to a compound/agent which increases the bulk mass of a composition. Examples of bulking agents include, without limitation, glycine, glutamic acid, alanine, mannitol, hydroethyl starch, dextran, PVP (poly vinyl pyrrolidone), mannitol, sorbitol, oligosaccharide-derived sugar alcohol, maltitol, lactitol, maltotriitol, xylitol, polyethylene glycol, sucrose, glucose, maltose, xorbitol, NaCl, or any combination thereof. These agents can also serve as tonicity modifiers. In embodiments, the concentration of bulking agent is from about 50 mM to about 300 mM; or from about 100 mM to about 200 mM, or about 150 mM, or from about 50 mM to about 150 mM, or about 108 mM, or about 54 mM.

In an embodiment, the tonicity modifier and the bulking agent are in concentrations such that the tonicity modifier/bulking agent ratio is about 1.0 to about 15.0 (wt/wt); from about 1.0 to about 10.0, about 3.0 to about 10.0, about 5.0 to about 10.0, for example about 5.0, about 8.0, or about 10.0. In an embodiment, the concentration of bulking agent is adjusted based on the concentration of the tonicity modifier so that the tonicity modifier/bulking agent ratio is in the desired range.

In embodiments, the composition further comprises one or more additional pharmaceutically acceptable ingredients such as carriers, excipients, diluents, stabilizers, buffers and the like.

In an embodiment, the pharmaceutical composition further comprises a sugar, for example a reducing and/or a non-reducing sugar. As used herein, a "reducing sugar" is one which contains a hemiacetal group that can reduce metal ions or react covalently with lysine and other amino groups in proteins and a "non-reducing sugar" is one which does not have these properties of a reducing sugar. In an embodiment, the reducing sugar is fructose, mannose, maltose, lactose, arabinose, xylose, ribose, rhamnose, galactose, glucose or any combination thereof. In an embodiment, the non-reducing sugar is sucrose, trehalose, sorbose, melezitose, raffinose or any combination thereof. In an embodiment, the pharmaceutical composition of the present invention is lyophilized in the presence of a reducing sugar. In an embodiment, the pharmaceutical composition of the present invention is lyophilized in the presence of a non-reducing sugar.

In embodiments, the pharmaceutical composition of the present invention has an osmolality of about 180 mOsm to about 350 mOsm; or of about 250 mOsm to about 350 mOsm, or of about 200 mOsm to about 300 mOsm. In certain embodiments, for example when the present composition is prepared for lyophilisation, it may have an osmolality higher than 350 mOsm. In such a case, the reconstituted solution may have a volume superior than the volume of the composition in order to dilute the components and reduce the osmolality. Also, when the composition is designed for the administration of a small volume, the osmolality of the composition may be higher than 350 mOsm.

As used herein, a "stabilising agent" refers to an agent that stabilises plasminogen in solution. In an embodiment, the stabilising agent comprises an amino acid, an amino acid salt, an amino acid analog or any mixture thereof. In a further embodiment, the amino acid, amino acid salt, amino acid analog or mixture thereof is arginine, proline, glutamic acid, aspartic acid, glycine, alanine, cysteine, lysine, a lysine analog such as epsilon-amino caproic acid, or any combination thereof. In a preferred embodiment, said amino acid can be in the form of an amino acid base such as arginine hydrochloride and lysine hydrochloride. In an embodiment, the pharmaceutical composition comprises two amino acids, amino acid salts and/or amino acid analogs. In another embodiment, the pharmaceutical composition comprises three amino acids, amino acid salts and/or amino acid analogs. In embodiments, the concentration of amino acid is from about 10 mM to about 300 mM, from about 20 mM to about 200 mM, or from about 10 mM to about 100 mM, or from about 25 mM to about 75 mM, or about 10 mM, or about 25 mM, or about 50 mM, or about 75 mM, or about 100 mM, about 150 mM, about 200 mM, about 250 mM, or about 300 mM.

In another embodiment, the pharmaceutical composition of the present invention further comprises an antioxidant. In an embodiment, the antioxidant is methionine, oxidized glutathione (Glu-Cys-Gly)$_2$ (613 kDa), ascorbic acid, N-acetyl-L-cysteine/homocysteine, glutathione, 6-hydroxy-2,5,7,8-tetramethylchroman-2-carboxylic acid (Trolox®), lipoic acid, sodium thiosulphate, platinum, glycine-glycine-histidine (tripeptide), butylated hydroxyltoluene (BHT), or any combination thereof. In embodiments, the concentration of the antioxidant is from about 10 mM to about 200 mM, e.g., about 10 mM, about 50 mM, about 100 mM, about 150 mM, or about 200 mM.

In another embodiment, the pharmaceutical composition of the present invention further comprises a surfactant. As used herein, a "surfactant" refers to a compound/agent that reduces interfacial tension between a liquid and a solid when dissolved in solution. In an embodiment, the surfactant is Polysorbate® 80, Polysorbate® 20, Pluronic® F-68, or Brij® 35; poloxamers (e.g. poloxamer 188 or Pluronic® F-68); Triton®; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, or copolymers of ethylene and propylene glycol, or any combination thereof. In an embodiment, the concentration of surfactant is adjusted to reduce aggregation of the plasminogen, biologically active variant or fragment thereof and/or minimizes the formation of particulates in the composition and/or reduces adsorption. In an embodiment, the surfactant is present in the composition in a concentration of about 0.001-1% (w/v), about 0.002% to about 0.02% (w/v), or about 0.002% to about 0.006% (w/v). In some embodiments, the composition comprises a surfactant which is a poloxamer. In some embodiments, the composition comprises Pluronic® F68. In particular embodiments, the composition comprises from about 0.01% (w/v) to about 1% (w/v) of Pluronic® F68, for example about 0.1% (w/v) of Pluronic® F68. In an embodiment, the composition is substantially free or free of nonionic surfactant, e.g., the composition comprises less than about 0.02%, 0.01%, 0.006%, or 0.004% (w/v) of nonionic surfactant.

In another embodiment, the pharmaceutical composition of the present invention further comprises a polymeric stabilizer. In an embodiment, the polymeric stabilizer is Heparin (6 to 30 kDa); Polyaminoacid (2 to 100 kDa) such as Poly (Glu), Poly (Asp), and Poly (Glu, Phe); Carboxymethyl cellulose (10-800 cps); Cyclodextrin; Dextran Sulphate, or any combination thereof. In embodiments, the concentration of the polymeric stabilizer is from about 0.001% to about 0.50%, or from about 0.001% to about 0.25%.

In another embodiment, the pharmaceutical composition of the present invention further comprises a polyethylene glycol, e.g., PEG 200, PEG 400, PEG 1000, PEG, 4000, PEG, 8000, PEG 10 000, or any combination thereof. In an embodiment, the concentration of the polyethylene glycol is from about 0.5% to about 10% (w/w).

In an embodiment, the pharmaceutical composition of the present invention further comprises a preservative. As used herein, a "preservative" refers to a compound/agent which can be added to the pharmaceutical composition to essentially reduce bacterial activity therein, thus facilitating the production of a multi-use pharmaceutical composition, for example. Examples of preservatives include m-cresol, benzyl alcohol, methanol, ethanol, iso-propanol, butyl paraben, ethyl paraben, methyl paraben, phenol, glycerol, xylitol, resorcinol, catechol, 2,6-dimethylcyclohexanol, 2-methyl-2,4-pentadiol, dextran, polyvinylpyrrolidone, 2-chlorophenol, benzethonium chloride, merthiolate (thimersosal), benzoic acid (propyl paraben) MW 180.2, benzoic acid MW 122.12, benzalkonium chloride, chlorobutanol, sodium benzoate, sodium propionate, or cetylpyridinium chloride. The preservative is selected for compatibility with the buffer and other components of the pharmaceutical composition (i.e., the solution is clear). For example, when the buffer is sodium acetate or sodium phosphate, compatible preservatives include methanol, ethanol, iso-propanol, glycerol, resorcinol, 2-methyl-2,4-pentadiol, merthiolate (thimerosal), benzalkonium chloride, sodium benzoate, or cetylpyridinium chloride. The concentration of the preservative used in the present composition can be determined according to the judgment of those of skill in the art. In some embodiments, the concentration of the preservative is about 0.005 to about 10% (w/v), about 0.1 to about 1.0% (w/v), or about 0.3 to about 0.7% (w/v). In some embodiments, the concentration of the preservative is about 0.005, 0.1, 0.3, 0.5, 0.7, or 1.0% (w/v).

In another embodiment, the pharmaceutical composition of the present invention is free of preservative.

One or more additional pharmaceutically acceptable carriers, excipients or stabilizers, such as those described in Remington's Pharmaceutical Sciences 19$^{th}$ edition, Genarro, A. Ed. (1995) can be included in the present composition provided that they do not significantly adversely affect the desired characteristics of the pharmaceutical composition of the invention. Additional constituent elements of the composition of the present invention can include water, e.g., water for injection, vegetable oil, a thickening agent such as methylcellulose, an anti-adsorbant, a wetting agent, antioxidants including ascorbic acid and methionine, chelating agents such as EDTA, metal complexes (e.g. Zn-protein complexes), biodegradable polymers such as polyesters, and/or salt-forming counter-ions such as sodium etc. Acceptable carriers, excipients or stabilizers are present in an amount such that they are nontoxic to subjects at the dosages and concentrations employed.

In an embodiment, the pharmaceutical composition of the present invention has a total weight of solid of from about 3.5% to about 8% when lyophilized, preferably from about 3.5% to about 6%, and more preferably of from about 3.8% to about 5.5%. Increasing the concentration of components in the pharmaceutical composition of the invention results in increasing the total % of solid in the lyophilized composition and improving the cake appearance of the lyophilised composition.

In an embodiment, plasminogen or a variant thereof is Lys-plasminogen or Glu-plasminogen. In another embodiment, plasminogen or a variant thereof is Glu-plasminogen. In an embodiment, plasminogen or a variant thereof is composed various types of plasminogen and/or variants. Preferably, the content of Glu-plasminogen represents more than 50% of the total content of plasminogen or variants thereof, or more than 60%, or more than 70%, or more than 80%, or more than 90%.

An embodiment of the present invention is a pharmaceutical composition comprising plasminogen or a variant thereof, wherein the total amount of protein other than the plasminogen or variant thereof in the composition is less than about 10%, less than about 5%, or less than about 2%. An embodiment of the present invention is a pharmaceutical composition comprising plasminogen or a variant thereof, wherein the composition does not comprise or is substantially free of, an additional protein (i.e. in addition to the plasminogen or variant thereof). In an embodiment of the present invention, the composition does not comprise or is substantially free of albumin. In an embodiment of the present invention, the composition does not comprise or is substantially free of aprotinin. In an embodiment of the present invention, the composition does not comprise or is substantially free of a trypsin inhibitor. In an embodiment of the present invention, the composition does not comprise or is substantially free of a serine protease inhibitor. In an embodiment of the present invention, the composition does not comprise or is substantially free of plasmin. In an embodiment of the present invention, the composition is substantially free or free of a surfactant, i.e. the concentration of surfactant is less than 0.01 mM.

In an embodiment, the pharmaceutical composition comprising plasminogen of the present invention is stable at room temperature for at least 2 hours, 24 hours, a week or a month.

In an embodiment, the pharmaceutical composition comprising plasminogen of the present invention is stable at temperature below 0° C. for at least 3 months, for at least 6 months, for at least 12 months or for at least 24 months. Said temperature below 0° C. is about −20° C., about −30° C., about −60° C., about −70° C. or about −80° C.

In embodiments, the pharmaceutical composition comprising plasminogen is a liquid composition, a liquid composition suitable for lyophilisation, a liquid composition suitable for freezing, a lyophilised composition, a frozen composition or a reconstituted composition.

The term "pharmaceutical composition" designates a composition for pharmaceutical, medical or therapeutic purposes.

All combinations of the components described herein (pH, buffer, tonicity modifier, bulking agent, stabilising agent, etc.) and their respective concentrations for the pharmaceutical composition of the present invention are specifically envisioned by the present disclosure. Representative examples of pharmaceutical compositions of plasminogen (Pg) according to the present invention are represented in Table 1A.

TABLE 1A

| No. | Pg | Buffer | Bulking agent | Stabilising agent | Tonicity modifier | pH |
|---|---|---|---|---|---|---|
| 1 | 5 mg/ml | 10 mM Citrate | 73 mM Sucrose | 67 mM Glycine | 68.4 mM NaCl; | 6.5 |
| 2 | 5 mg/ml | 10 mM Citrate | 73 mM Sucrose | 33.5 mM Glycine | 34.22 mM NaCl | 6.5 |
| 3 | 5 mg/ml | 10 mM Citrate | 117 mM Sucrose | 67 mM Glycine | 68.4 mM NaCl; | 6.5 |
| 4 | 5 mg/ml | 10 mM Citrate | 117 mM Sucrose | 67 mM Glycine | 34.22 mM NaCl | 6.5 |
| 5 | 5 mg/ml | 10 mM Citrate | 73 mM Sucrose | 67 mM Glycine | 34.22 mM NaCl | 6.5 |
| 6 | 5 mg/ml | 10 mM Citrate | 73 mM Sucrose | 67 mM Glycine | 75.3 mM NaCl | 6.5 |
| 7 | 5 mg/ml | 10 mM Citrate | 79 mM Sucrose | 40 mM Glycine | 75 mM NaCl | 6.5 |
| 8 | 5 mg/ml | 10 mM Citrate | 77 mM Sucrose | 47 mM Glycine | 75 mM NaCl | 6.5 |
| 9 | 5 mg/ml | 10 mM Citrate | 75 mM Sucrose | 54 mM Glycine | 75 mM NaCl | 6.5 |
| 10 | 5 mg/ml | 10 mM Citrate | 50-150 mM Sucrose | 25 to 75 mM Glycine | 35-150 mM NaCl | 6.5 |
| 11 | 5 mg/ml | 10 mM Citrate | 50-150 mM Mannitol | 25 to 75 mM Glycine | 35-150 mM NaCl | 6.5 |
| 12 | 5 mg/ml | 10 mM Citrate | 50-150 mM Sorbitol | 25 to 75 mM Glycine | 35-150 mM NaCl | 6.5 |
| 13 | 5 mg/ml | 10 mM Citrate | 50-150 mM Sucrose | 25 to 75 mM Arginine | 35-150 mM NaCl | 6.5 |
| 14 | 5 mg/ml | 10 mM Citrate | 50-150 mM Mannitol | 25 to 75 mM Arginine | 35-150 mM NaCl | 6.5 |
| 15 | 5 mg/ml | 10 mM Citrate | 50-150 mM Sorbitol | 25 to 75 mM Arginine | 35-150 mM NaCl | 6.5 |
| 16 | 5 mg/ml | 10 mM Phosphate | 50-150 mM Sucrose | 25 to 75 mM Glycine | 35-150 mM NaCl | 7.2 |
| 17 | 5 mg/ml | 10 mM Phosphate | 50-150 mM Mannitol | 25 to 75 mM Glycine | 35-150 mM NaCl | 7.2 |
| 18 | 5 mg/ml | 10 mM Phosphate | 50-150 mM Sorbitol | 25 to 75 mM Glycine | 35-150 mM NaCl | 7.2 |
| 19 | 5 mg/ml | 10 mM Phosphate | 50-150 mM Sucrose | 25 to 75 mM Arginine | 35-150 mM NaCl | 7.2 |
| 20 | 5 mg/ml | 10 mM Phosphate | 50-150 mM Mannitol | 25 to 75 mM Arginine | 35-150 mM NaCl | 7.2 |
| 21 | 5 mg/ml | 10 mM Phosphate | 50-150 mM Sorbitol | 25 to 75 mM Arginine | 35-150 mM NaCl | 7.2 |

Other representative examples of pharmaceutical compositions according to the present invention are represented in Table 1B below for compositions of about 0.01 mg/ml to about 80 mg/ml and preferably from 5 to 60 mg/ml of plasminogen or variant thereof and having a pH from 6.5 to 8.0. In all these examples, the content of plasminogen is preferably mainly composed of Glu-plasminogen, and the total content of plasminogen or variants is from 5 mg/mL to 60 mg/mL.

TABLE 1B

| No. | Bulking agent | Stabilising agent | Tonicity modifier |
|---|---|---|---|
| 1 | — | — | 35 mM NaCl |
| 2 | — | 25 mM Arginine HCl | 35 mM NaCl |
| 3 | — | 50 mM Arginine HCl | 35 mM NaCl |
| 4 | 50 mM Mannitol | 25 mM Arginine HCl | 35 mM NaCl |
| 5 | 50 mM Mannitol | 50 mM Arginine HCl | 35 mM NaCl |
| 6 | 100 mM Mannitol | 25 mM Arginine HCl | 35 mM NaCl |
| 7 | 100 mM Mannitol | 50 mM Arginine HCl | 35 mM NaCl |
| 8 | 50 mM Sorbitol | 25 mM Arginine HCl | 35 mM NaCl |
| 9 | 50 mM Sorbitol | 50 mM Arginine HCl | 35 mM NaCl |
| 10 | 100 mM Sorbitol | 25 mM Arginine HCl | 35 mM NaCl |
| 11 | 100 mM Sorbitol | 50 mM Arginine HCl | 35 mM NaCl |
| 12 | — | — | 50 mM NaCl |
| 13 | — | 25 mM Arginine HCl | 50 mM NaCl |
| 14 | — | 50 mM Arginine HCl | 50 mM NaCl |
| 15 | 50 mM Mannitol | 25 mM Arginine HCl | 50 mM NaCl |
| 16 | 50 mM Mannitol | 50 mM Arginine HCl | 50 mM NaCl |
| 17 | 100 mM Mannitol | 25 mM Arginine HCl | 50 mM NaCl |
| 18 | 100 mM Mannitol | 50 mM Arginine HCl | 50 mM NaCl |
| 19 | 50 mM Sorbitol | 25 mM Arginine HCl | 50 mM NaCl |
| 20 | 50 mM Sorbitol | 50 mM Arginine HCl | 50 mM NaCl |
| 21 | 100 mM Sorbitol | 25 mM Arginine HCl | 50 mM NaCl |
| 22 | 100 mM Sorbitol | 50 mM Arginine HCl | 50 mM NaCl |
| 23 | — | 25 mM Arginine HCl | — |
| 24 | — | 50 mM Arginine HCl | — |
| 25 | — | 75 mM Arginine HCl | — |
| 26 | — | 100 mM Arginine HCl | — |
| 27 | — | 25 mM Arginine HCl | — |
| 28 | — | 50 mM Arginine HCl | — |
| 29 | — | 75 mM Arginine HCl | — |
| 30 | — | 100 mM Arginine HCl | — |

In an embodiment, the pharmaceutical composition comprising plasminogen of the present invention is suitable for intravenous, subcutaneous, topical, intradermal, ophthalmic and/or intramuscular administration.

According to an embodiment, the pharmaceutical composition of the present invention is for administration in a human subject. Preferably, the pharmaceutical composition of the present invention is for intravenous, subcutaneous, topical, intramuscular or ophthalmic administration. In an embodiment, the composition of the present invention is in the form of a liquid, gel, cream, or ointment.

The plasminogen that is formulated in the composition of the present invention may be obtained from several sources. It may be obtained by recombinant synthesis, or extracted/purified from blood, plasma or a blood-derived solution. Plasminogen can be extracted from blood or plasma by Cohn fractionation or by precipitation. Plasminogen can be purified from plasma or blood-derived solution by a binding affinity chromatography, such as the method described in WO 2006/120423. A variant of plasminogen includes, without limitation, any modifications of the amino acid sequence or any additions of a group thereto or any additions of an amino acid or an amino acid sequence thereto. A fragment of plasminogen includes, without limitation, any deletions of an amino acid or an amino acid sequence thereto.

As used herein, the term "about" intends to cover + or −10% of the corresponding value.

The term "subject" includes living organisms which can benefit from an administration of plasminogen, a variant thereof or a fragment thereof. The term "subject" includes animals such as mammals or birds. Preferably, the subject is a mammal. More preferably, the subject is a human. Most preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a composition of the invention to a subject (or application or administration of the composition of the invention to a tissue or an organ of a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required.

As used herein, the term "therapeutically effective amount" means the amount of compound that, when administered to a subject for treating or preventing a particular disorder, disease or condition, is sufficient to effect such treatment or prevention of that disorder, disease or condition. As used herein, the term "therapeutically effective amount" further means the amount of plasminogen, its variant or its fragment that is effective to heal a wound, heal a tympanic membrane perforation, heal a periodontal wound, treat an infectious disease, increase or maintain oral health, treat posterior vitreous detachment (PVD), diabetic ulcer, and plasminogen-deficient subjects thrombolysis indications, such as coronary thrombosis, treating reperfusion injury to tissue, treating ischemia, infarction, brain edema, for improving the microcirculation, treat plasminogen-deficient subjects, and modulate of complement pathway in subjects. Dosages and therapeutically effective amounts may vary for example, depending upon a variety of factors including the activity of the age, body weight, general health, gender, and diet of the subject, the time of administration, the route of administration, the rate of excretion, and any drug combination, if applicable, the effect which the practitioner desires the compound to have upon the subject, and the particular disorder(s) the subject is suffering from. In addition, the therapeutically effective amount may depend on the subject's blood parameters (e.g., lipid profile, insulin levels, glycemia), the severity of the disease state, organ function, or underlying disease or complications. Such appropriate doses may be determined using any available assays including the assays described herein. When the pharmaceutical composition of the invention is to be administered to humans, a physician may for example, prescribe a relatively low dose at first, subsequently increasing the dose until an appropriate response is obtained. The dose to be administered will ultimately be at the discretion of the physician.

Kits

The compound(s) of the invention may be packaged as part of a kit, optionally including a container (e.g., packaging, a box, a vial, etc.). The kit may be commercially used according to the methods described herein and may include instructions for use in a method of the invention.

The composition of the invention may or may not be administered to a patient at the same time than another active ingredient, before or after, and by the same route of administration or by another route of administration. Therefore, the present invention also encompass kits which, when used by the medical practitioner, can simplify the administration of appropriate amounts of the present composition alone or in combination with another active ingredient to a patient.

Kits of the invention can further comprise a pharmaceutically acceptable liquid for reconstitution of a lyophilised composition. For example, if an active ingredient is provided in a solid form that must be reconstituted for parenteral administration, the kit can comprise a sealed container of a suitable pharmaceutically acceptable liquid in which the active ingredient can be dissolved to form a particulate-free sterile solution that is suitable for parenteral administration.

In certain embodiments, the present composition is contained in a vial, bottle, tube, syringe or other container for single or multiple administrations. Such containers can be made of glass or a polymer material such as polypropylene, polyethylene, polyvinylchloride, or polyolefin, for example. In some embodiments, the containers can include a seal, or other closure system, such as a rubber stopper that can be penetrated by a needle in order to withdraw a single dose and then re-seal upon removal of the needle. All such containers for injectable liquids, lyophilized compositions, reconstituted lyophilized compositions or powders for reconstitution and injection known in the art are contemplated for use in the presently disclosed compositions and methods. In a particular embodiment, the container is a pen-type delivery apparatus comprising a single dose or multiple doses. Such a pen-type delivery apparatus can be permanent, e.g., a permanent pen that houses a disposable cartridge containing a single dose or multiple doses, or the entire apparatus can be disposable, e.g., a disposable pen that contains a single dose or multiple doses. In certain embodiments where the pen-type delivery apparatus comprises multiple doses, the dose can be pre-set, i.e., fixed. In other embodiments, the dose can be a flexible dose, i.e., dialed-in by the user. In some embodiments, the pen-type delivery apparatus comprises a luer-lock, luer-cone, or other needle fitting connector that facilitates attachment of a disposable needle. In other embodiments, the pen-type delivery apparatus comprises a staked, i.e., permanent needle. In another particular embodiment, the container is a syringe. In some embodiments, the syringe comprises a luer-lock, luer-cone, or other needle fitting connector that facilitates attachment of a disposable needle. In other embodiments, the syringe comprises a staked, i.e., permanent, needle. In some embodiments, the syringe is prefilled with a single dose or multiple doses.

Stability Assays

"Stable" compositions include compositions in which the protein (plasminogen or variant thereof) therein essentially retains its physical stability and/or chemical stability and/or biological activity upon storage. Various analytical techniques for measuring protein stability are available in the art and are reviewed in Lee, V., 1991, Peptide and Protein Drug Delivery, 247-301 (Marcel Dekker, Inc., New York, N.Y.) and Jones, A. 1993, Adv. Drug Delivery Rev. 10: 29-90, for example. Stability can be measured at a selected temperature for a selected time period. In an embodiment, the composition is stable at room temperature (about 25° C.) or at 40° C., for at least 1, 2, 3, 4, 5 or 6 months and/or stable at about 2-8° C. for at least 1, 2, 3, 4, 5 or 6 months. Furthermore, in certain embodiments, the composition is stable following freezing (e.g., −30° C.). In certain embodiments, the criteria for stability are as follows: (1) the composition remains clear by visual analysis; (2) the concentration, pH and osmolality of the composition has no more than about ±10% change; (3) no more than about 10%, no more than about 5%, or no more than about 1% of aggregate forms as measured by SEC-HPLC; and (4) no more than 10%, no more than about 5%, or no more than 3% of plasminogen breaks down as measured by known in the art and well established analytical methods.

Thermal Denaturation:

The thermal denaturation experiments HTS formulation screening for Plasminogen or a variant thereof or a fragment thereof can performed using Optim 2™ from Pall; or other alternative biophysical technique(s) to monitor the unfolding of the protein (Standard PCR (with a heating block), Fluorimeter or CD spectrophotometer (with temperature control). As an example, the Optim 2 system simultaneously measure a range of protein stability-indicating parameters including unfolding transition temperature (Tm), aggregation onset temperature (Tagg) and rates of aggregation.

The Effects of Excipients on the Thermostability:

Narrow pH is determined at the optimum pH range with higher Melting Temperature (Tm) and Aggregation Onset Temperature (Tagg). If the higher Tm is obtained in the physiological range of 6.5-7.5; the next test(s) is to screen with at least 3 buffer system(s).

Additionally, IEF (isoelectric focusing) or cIEF (capillary isoelectric focusing) can be tested for evaluation the physical conformation of plasminogen in solution.

The percentage of stabilization based on plasminogen enzyme activity measurements, for each buffer/excipient and for a reference solution containing only plasminogen after 1-8 hours of incubation at 60° C. In another test, the stabilization may be evaluated at 37° C. for 1-8 hours. The percentage of stabilization is calculated as:

Percent of Stabilization=100×[$S-T$]/[$T$]

Where S is the residual enzyme activity of the enzyme solution with the excipient to be tested after 10 days at 35° C.; and T is the activity of the reference without any excipient stored in the same conditions.

Aggregation and Particle Measurement Count (PMC):

The PMC is calculated by the Light Obscuration Particle Count Test. Analysts should use a suitable instrument that is based on the principle of light blockage and that allows an automatic determination of particle size and number. The sensor selected must be appropriate for the intended particle size range and anticipated particle count. Standards particle size range are generally between 2 and 100 mm. Analysts should verify the performance of the apparatus using the USP Particle Count RS dispersed in particle-free water at an appropriate volume. Care must be taken to avoid agglomeration of particles during dispersion in the calibration process.

Methods: Product samples are tested in the manner that most suitably represents delivery (e.g., expelled syringe contents). For parenterals that have a sufficient volume (i.e., volume large enough to facilitate testing), testing of individual units is often diagnostic. For parenteral products that do not have a sufficient volume, carefully and thoroughly mix each unit, then combine the contents of a suitable number of units in a separate container to obtain the volume required for a single test (generally 0.2-5.0 mL). If a dilution is performed, ensure that the blank container has sufficient volume for product and diluents and that few, if any, particles are introduced in the process. Open each unit cautiously, remove the sealing closure, and avoid contamination of the contents before sampling, diluting, or, if necessary, pooling. When a product solvent is specified, e.g., for lyophilized solids or powders for parenteral use, the reconstitution or dilution must be performed with the appropriate amount of specified solvent. In this case, the solvent itself may be tested to ensure that it is not a significant source of particles. Subtraction of the solvent particle count from the total count is not allowed. Eliminating gas bubbles is a key step, especially for proteinaceous products that readily entrain gas. Two methods are recommended: either allowing the product fluid to stand under ambient pressure or applying a gentle (e.g., 75 Torr) vacuum. Other methods may be used when demonstrated to be suitable. Sonication should be avoided. Once the samples have been degassed, they must be remixed gently to suspend all particles by mixing the contents of the sample gently but thoroughly by an appropriate means, e.g., slow swirling of the container by hand. Inversion to mix the product fluid is not recommended at any time. Immediately after mixing, withdraw NLT four aliquots, each of a volume appropriate for the instrument's capacity (generally 0.2-5.0 mL). Count the number of particles over the selected size range, including particles equal to or greater than 10 and 25 mm. Disregard the result obtained for the first aliquot, and calculate the mean number of particles at each size range for the remaining aliquots of the preparation being tested. A tare volume also can be applied to control sampling that should be representative of the sensor dynamic range and needle volume.

Evaluation: Regulatory authorities like the FDA (Food and Drug Administration) and USP/EP/JP (United State Pharmacopoeia) Chapters (787, 788 and 789), EP European Pharmacopoeia (2.9.20 Particulate Contamination), and JP Japanese Pharmacopoeia JP (16: 6.06. 6.07 Foreign Insoluble Matter Test) requirements on Particulate Matter define the acceptable level of particles in liquid preparation for human use as follow. For parenteral products that are therapeutic protein injections for infusion or injection supplied in containers with a nominal content of less than or equal to 100 mL: the average number of particles present in the units tested should not exceed 6000 per container equal to or greater than 10 µm and should not exceed 600 per container equal to or greater than 25 µm. For therapeutic protein injections supplied in containers with a nominal content of more than 100 mL, and parenteral infusion preparations or injections with a nominal content of more than 100 mL: the average number of particles present in the units tested should not exceed 25 per mL equal to or greater than 10 µm and should not exceed 3 per mL equal to or greater than 25 µm. Also, total particle load should not exceed 6000 per container equal to or greater than 10 µm and should not exceed 600 per container equal to or greater than 25 µm. Products that are used with a final filter during administration (in-line) are exempt from these requirements, providing that scientific data are available to justify the exemption. However, filtrates are expected to comply with the guideline. For products supplied or first reconstituted in <100 mL, and then diluted for infusion in a volume >100 mL, particle content should be assessed both before and after dilution and evaluated based on their final volume. Hence, USP/EP/JP Method are herein included in this document. Herein, the term "Particle" refers to "Particulate" and vice-versa; these terms can be used intechangeably.

Kinetic Study Measured by Light Scattering at 476 nm/600 nm Using the Optim-2™ or by Standard UV Spectrophotometer at UV at 350 nm:

Accelerated conditions such as elevated temperature (65° C.) and acidic solution pH (4.5) or basic solution pH (9.5) is selected to more rapidly screen for different stabilizing excipients. The components of the composition are evaluated to increase the Tagg as a function of time at a fixed temperature (55-60° C.) for at least 1 to 4 hours. The aggregation kinetic behavior of the Plasminogen solution is measured at 55-60° C. equipped with temperature control (onset Tm is determined) for up to 4 h. The excipients are screened for their effect on inhibition of Plasminogen aggregation as measured by the light scattering at 267 nm, 467 nm or 350 nm (Cheng, W. et al. "Comparison of High-Throughput Biophysical Methods to Identify Stabilizing Excipients for a Model IgG2 Monoclonal Antibody:Conformational Stability and Kinetic Aggregation Measurements" Journal of Pharmaceutical Sciences, Vol. 101, No 5, page 1701-1720, 2012).

The Effect of Protein Concentration of Thermal Stability:

One of the advantages of Optim-2™ or Dual Scanning Fluorimeter (DSF with the Sypro Dye) is the ability to carry out measurements of Tm and Tagg in highly concentrated protein solutions. Whether investigating potential candidates for relative stability, or screening different formulation conditions for stabilization of proteins, it may be important to identify the properties of the protein solution at high concentrations where the number of characterization methods available is limited.

The Effect of Formulation Composition on the Final Osmolality:

In the final pharmaceutical composition, the buffer, excipient and salt concentrations are not preferred to be very high due to the practical limitations of parental injection. Instead, more moderate concentrations such as more physiological are preferred in order to obtain an Osmolality in the range of 240 to 400 mOsm. Therefore, Osmolality is calculated to initially determine this range; however for IV injection a higher Osmolality concentrations can be also be used during the development of the freeze drying process if after reconstitution Plasminogen or variant or fragment thereof is diluted by the solution for reconstitution.

It should be noted that the term "Formulation" and "Composition" may be used herein alternatively and are intended to designate the same.

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

EXAMPLES

The following examples further illustrate the practice of this invention but are not intended to be limiting thereof.

Example 1: Stability of Plasminogen in a Frozen Formulation

Stability testing results for a pharmaceutical composition comprising 5 mg/ml of human plasminogen extracted from plasma in accordance with a binding affinity technique described in WO 2006/120423, 10 mM Citrate, 150 mM NaCl, at pH 6.5 (Lot: 2002.pc02_Pg140210.01) were stored at −20° C., −30° C. and −80° C. for up to 6 Months. The stability data indicated that plasminogen is stable under these frozen conditions. Plasminogen lot: 2002.pc02_Pg140210.01 was tested at −20° C., −30° C. and −80° C. The level of aggregation was investigated by SEC-HPLC, the level of purity by SDS-PAGE under reducing, and also under non-reducing conditions, the level of activity by BCS activity and the protein concentration by absorbance at 280 nm ($ABS_{280}$). The results of the stability data after 6 months demonstrated that all the stability indicating assays achieved the desired specifications.

Example 2: Osmolality Analysis and Total Percentage of Solid Analysis

The osmolality of formulations 1 to 6 and the total percentage of solid after lyophilisation for formulations 1-9 are reported in Table 2. The content of Formulations 1-9 is defined in Table 1A.

TABLE 2

| Formulation # | Plasminogen mg/mL | Sucrose mM | Glycine mM | NaCl mM | Total % of Solid Cake % | Osmolality mOsm |
|---|---|---|---|---|---|---|
| 1 | 5 | 73 | 67 | 68 | 3.9 | 265 |
| 2 | 5 | 73 | 34 | 34 | 3.4 | 198 |
| 3 | 5 | 117 | 67 | 68 | 5.4 | 309 |
| 4 | 5 | 117 | 67 | 34 | 5.2 | 275 |
| 5 | 5 | 73 | 67 | 34 | 3.7 | 231 |
| 6 | 5 | 73 | 67 | 75 | 3.9 | 272 |
| 7 | 5 | 27 | 40 | 75 | 3.9 | TBD |
| 8 | 5 | 26.5 | 47 | 75 | 3.9 | TBD |
| 9 | 5 | 26 | 54 | 75 | 3.9 | TBD |

The osmolality is in the physiological range of 240-400 mOsm. The resulting osmolality of the tested compositions are advantageously falling within or very close to the physiological range of osmolality. The total % of solid cake (g of solid composition after lyophilisation per 100 ml of the liquid composition before lyophilization) is around 4% for all compositions and placebos, which is within the preferred range of 3.5 to 8%.

Example 3: Molecular Weight of Plasminogen

The molecular weight of the plasminogen purified and formulated in the pharmaceutical composition of the present invention has a molecular weight of 87,000 (MW), determined by calculation of the primary sequence of amino acids of the plasminogen and verified by mass spectrometry.

Example 4: Study of Appearance of the Cake after Lyophilisation

Formulations 1 to 5 have been lyophilised following the cycle process detailed in Table 5. The content of Formulations 1-5 is defined in Table 1A.

TABLE 5

| Step | Shelf Temperature Set Point, [° C.] | Ramp Time, [minutes] | Soak Time, [minutes] | Pressure Set Point, [mT] |
|---|---|---|---|---|
| Product Loading | 5 | — | 60 | Atmospheric |
| Freezing | −50 | 120 | 240 | Atmospheric |
| Evacuation | −50 | — | — | 50 |
| Primary | −22 | 90 | 3860 | 50 |
| Secondary | 35 | 120 | 270 | 50 |

FIGS. 2 to 11 are pictures of the vials containing 12.5 ml of Formulations 1 to 5 respectively, or their corresponding placebo (without plasminogen). Thus, the effect of the presence of plasminogen on the stability of the composition has been investigated. The physical inspection of the appearance of the cake that has been formed by the lyophilisation process. All cakes have maintained a uniform density, without any discoloration. Less than 10% of the tested vials for the placebo of Formulations 2, 3 and 5 have provided a melt back. Less than 10% of the tested vials for the placebo of Formulation 1 have collapsed. Less than 10% of the tested vials for the Formulations 1-5 and the placebo of Formulation 4 have shown a basal retraction. Overall the appearance of the cake is satisfying.

The content of the composition dictates collapse temperature. Each pure amorphous excipient has a characteristic Tg' and collapse temperature; the collapse temperature for the formulation is the mass averaged temperatures of all of the compositions in the amorphous phase. It is important to design a formulation with maximum collapse temperature, because the rate of drying is directly proportional to the sample temperature during lyophilization.

Finally, collapse temperature will be decreased if salts (NaCl) and excipients are not maximally crystallized. For example, glycine has a Tg' of −45° C., and its contribution to the amorphous phase can reduce collapse temperature to impractically low values.

Example 5: Effect of Amino Acid on Plasminogen Aggregation in Solution

Plasminogen alone in water generates a number of plasminogen aggregates that is inacceptable by the FDA i.e. higher than 6000 particles of 10 µm or greater per 100 mL of composition (see Sample F0406 in Table 6). Various sucrose-based formulations have been developed to formulate plasminogen. Although most of these formulations succeed to meet the threshold of 6000 particles of 10 µm or greater per 100 mL, formulations containing a lower particle content have been developed and the effect of amino acid to stabilise plasminogen is studied herein. These further formulations contain 10 mg of plasminogen and 35 mM NaCl, and tree buffers/pH have been tested, i.e. 10 mM Sodium Citrate (pH 6.5), 10 mM Sodium Phosphate (pH 7.2) and 10 mM Tris HCL (pH 8.0). Have been compared the presence and absence of an amino acid selected from arginine, alanine and glycine at a concentration of 0.5%. The tested formulations are fresh, i.e. before lyophilisation. Table 6 reports the PMC counts for the particles of 10 µm or greater and of 25 µm or greater. The presence of amino acid have shown a stabilizing effect has contributed to reduce the aggregation level.

TABLE 6

| Assigned Sample ID | Sample Description | Pre-Lyo PMC Count/mL | |
|---|---|---|---|
| | | 10 µm | 25 µm |
| F0406 | Pg Bulk in water at 10 mg/ml | 1,039,061 | 20,181 |
| Rx1 | Pg (5 mg/mL), 67 mM glycine | 5,793 | 155 |
| Rx5 | Pg (5 mg/mL), 12 mM citrate buffer, 73 mM sucrose, 68 mM NaCl, 67 mM glycine, pH 6.5 | 5,495 | 243 |
| Rx6 | Pg (5 mg/mL), 12 mM citrate buffer, 117 mM sucrose, 68 mM NaCl, pH 6.5 | 4,068 | 94 |
| Rx7 | Pg (5 mg/mL), 12 mM citrate buffer, 117 mM sucrose, 68 mM NaCl, pH 6.5 | 3,349 | 96 |
| F0080 | Pg (10 mg/mL), 10 mM Sodium Citrate, 35 mM NaCl, pH 6.5 | 147 | 0 |
| F0081 | Pg (10 mg/mL), 10 mM Sodium Citrate, 35 mM NaCl, 66 mM (0.5%) Glycine, pH 6.5 | 109 | 0 |
| F0082 | Pg (10 mg/mL), 10 mM Sodium Citrate, 35 mM NaCl, 28.5 mM (0.5%) Arginine, pH 6.5 | 122 | 1 |
| F0083 | Pg (10 mg/mL), 10 mM Sodium Citrate, 35 mM NaCl, 26 mM (0.5%) Alanine, pH 6.5 | 91 | 1 |
| F0102 | Pg (10 mg/mL), 10 mM Sodium Phosphate, 35 mM NaCl, pH 7.2 | 271 | 18 |
| F0103 | Pg (10 mg/mL), 10 mM Sodium Phosphate, 35 mM NaCl, 66 mM (0.5%) Glycine, pH 7.2 | 124 | 6 |
| F0104 | Pg (10 mg/mL), 10 mM Sodium Phosphate, 35 mM NaCl, 28.5 mM (0.5%) Arginine, pH 7.2 | 128 | 3 |
| F0105 | Pg (10 mg/mL), 10 mM Sodium Phosphate, 35 mM NaCl, 26 mM(0.5%) Alanine, pH 7.2 | 180 | 2 |
| F0106 | Pg (10 mg/mL), 10 mM Tris, 35 mM NaCl, pH 8.0 | 118 | 5 |
| F0107 | Pg (10 mg/mL), 10 mM Tris, 35 mM NaCl, 66 mM (0.5%) Glycine, pH 8.0 | 91 | 7 |
| F0108 | Pg (10 mg/mL), 10 mM Tris, 35 mM NaCl, 28.5 mM (0.5%) Arginine, pH 8.0 | 75 | 3 |
| F0109 | Pg (10 mg/mL), 10 mM Tris, 35 mM NaCl, 26 mM (0.5%) Alanine, pH 8.0 | 46 | 1 |

Example 6: Effect of Mannitol Combined with Amino Acid on Plasminogen Aggregation The presence of the bulking agent, 0.5% mannitol, on the formulations containing 10 mg of plasminogen and 35 mM NaCl, with either 10 mM Sodium Citrate (pH 6.5), 10 mM Sodium Phosphate (pH 7.2) or 10 mM Tris HCL (pH 8.0), with and without amino acid (0.5% arginine hydrochloride, alanine or glycine) have been tested and reported in Table 7. Fresh formulations (before lyo) were tested in this study. Generally, the presence of mannitol has lowered the particle counts. Generally, the combination of mannitol and amino acid contributes to lower the particle counts, and especially with the combination of arginine with mannitol.

TABLE 7

| Assigned Sample ID | Sample Description | Pre-Lyo PMC Count/mL 10 μm | 25 μm |
|---|---|---|---|
| F0114 | Pg (9 mg/mL), 10 mM Sodium Citrate, 35 mM NaCl, pH 6.5 | 3,610 | 61 |
| F0115 | Pg (9 mg/mL), 10 mM Sodium Citrate, 35 mM NaCl, 27 mM (0.5%) Mannitol, pH 6.5 | 805 | 8 |
| F0116 | Pg (9 mg/mL), 10 mM Sodium Citrate, 35 mM NaCl, 66 mM (0.5%) Glycine, 27 mM (0.5%) Mannitol, pH 6.5 | 962 | 13 |
| F0117 | Pg (9 mg/mL), 10 mM Sodium Citrate, 35 mM NaCl, 28.5 mM (0.5%) Arginine, 27 mM (0.5%) Mannitol, pH 6.5 | 520 | 11 |
| F0118 | Pg (9 mg/mL), 10 mM Sodium Citrate, 35 mM NaCl, 26 mM (0.5%) Alanine, 27 mM (0.5%) Mannitol, pH 6.5 | 990 | 1 |
| F0119 | Pg (9 mg/mL), 10 mM Sodium Phosphate, 35 mM NaCl, pH 7.2 | 133 | 6 |
| F0120 | Pg (9 mg/mL), 10 mM Sodium Phosphate, 35 mM NaCl, 27 mM (0.5%) Mannitol, pH 7.2 | 107 | 3 |
| F0121 | Pg (9 mg/mL), 10 mM Sodium Phosphate, 35 mM NaCl, 66 mM (0.5%) Glycine, 27 mM (0.5%) Mannitol, pH 7.2 | 191 | 6 |
| F0122 | Pg (9 mg/mL), 10 mM Sodium Phosphate, 35 mM NaCl, 28.5 mM (0.5%) Arginine, 27 mM (0.5%) Mannitol, pH 7.2 | 95 | 2 |
| F0123 | Pg (9 mg/mL), 10 mM Sodium Phosphate, 35 mM NaCl, 26 mM (0.5%) Alanine, 27 mM (0.5%) Mannitol, pH 7.2 | 113 | 5 |
| F0124 | Pg (9 mg/mL), 10 mM Tris, 35 mM NaCl, pH 8.0 | 86 | 2 |
| F0125 | Pg (9 mg/mL), 10 mM Tris, 35 mM NaCl, 27 mM (0.5%) Mannitol, pH 8.0 | 578 | 10 |
| F0126 | Pg (9 mg/mL), 10 mM Tris, 35 mM NaCl, 66 mM (0.5%) Glycine, 27 mM (0.5%) Mannitol, pH 8.0 | 163 | 5 |
| F0127 | Pg (9 mg/mL), 10 mM Tris, 35 mM NaCl, 28.5 mM (0.5%) Arginine, 27 mM (0.5%) Mannitol, pH 8.0 | 13 | 3 |
| F0128 | Pg (9 mg/mL), 10 mM Tris, 35 mM NaCl, 26 mM (0.5%) Alanine, 27 mM (0.5%) Mannitol, pH 8.0 | 119 | 8 |

Example 7: Effect of Preservative on Plasminogen Aggregation

The presence of preservative, such as 0.1% phenol, has been tested in the formulations containing 9 or 10 mg of plasminogen and 35 mM NaCl, with either 10 mM Sodium Citrate (pH 6.5), 10 mM Sodium Phosphate (pH 7.2) or 10 mM Tris HCL (pH 8.0), with 0.5% arginine hydrochloride or the combination of 0.5% arginine hydrochloride and 0.5% mannitol. Fresh formulations (before lyo) were tested in this study. The particle matter counts (PMC) have been reported in Table 8. Advantageously, the presence of phenol has not significantly affected the particle counts.

TABLE 8

| Assigned Sample ID | Sample Description | Pre-Lyo PMC Count/mL 10 μm | 25 μm |
|---|---|---|---|
| F0114 | Pg (9 mg/mL), 10 mM Sodium Citrate, 35 mM NaCl, pH 6.5 | 3,610 | 61 |
| F0143 | Pg (10 mg/mL), 10 mM Sodium Citrate, 35 mM NaCl, 28.5 mM (0.5%) Arginine, pH 6.5 | 609 | 8 |
| F0144 | Pg (10 mg/mL), 10 mM Sodium Citrate, 35 mM NaCl, 28.5 mM (0.5%) Arginine, 0.1% Phenol, pH 6.5 | 3,191 | 27 |
| F0145 | Pg (10 mg/mL), 10 mM Sodium Citrate, 35 mM NaCl, 28.5 mM (0.5%) Arginine, 27 mM (0.5%) Mannitol, 0.1% Phenol, pH 6.5 | 1,538 | 9 |
| F0155 | Pg (10 mg/mL), 10 mM Sodium Phosphate, 35 mM NaCl, 28.5 mM (0.5%) Arginine, pH 7.2 | 1,097 | 7 |
| F0156 | Pg (10 mg/mL), 10 mM Sodium Phosphate, 35 mM NaCl, 28.5 mM (0.5%) Arginine, 0.1% Phenol, pH 7.2 | 4,370 | 6 |
| F0157 | Pg (10 mg/mL), 10 mM Sodium Phosphate, 35 mM NaCl, 28.5 mM (0.5%) Arginine, 27 mM (0.5%) Mannitol, 0.1% Phenol, pH 7.2 | 747 | 9 |
| F0158 | Pg (10 mg/mL), 10 mM Tris, 35 mM NaCl, 28.5 mM (0.5%) Arginine, pH 8.0 | 169 | 4 |
| F0159 | Pg (10 mg/mL), 10 mM Tris, 35 mM NaCl, 28.5 mM (0.5%) Arginine, 0.1% Phenol, pH 8.0 | 168 | 3 |
| F0160 | Pg (10 mg/mL), 10 mM Tris, 35 mM NaCl, 28.5 mM (0.5%) Arginine, 27 mM (0.5%) Mannitol, 0.1% Phenol, pH 8.0 | 175 | 1 |

Several preservatives were compared. Table 9 reports comparison of 0.5% CMC, 0.1% phenol and 0.5% dextran within the formations formulations containing 10 mg of plasminogen and 35 mM NaCl, with either 10 mM Sodium Citrate (pH 6.5), 10 mM Sodium Phosphate (pH 7.2) or 10 mM Tris HCL (pH 8.0), and 0.5% arginine hydrochloride. Fresh formulations (before lyo) were tested in this study. The presence of dextran or phenol has not significantly affected the aggregation. However, CMC has significantly increased the aggregation. This is not surprising since CMC is known to increase the viscosity of a solution and is frequently used in the preparation of eye drop formulation.

TABLE 9

| Sample ID | Sample Description | Pre-Lyo PMC Count/mL | |
|---|---|---|---|
| | | 10 μm | 25 μm |
| F0119 | Pg (9 mg/mL), 10 mM Sodium Phosphate, 35 mM NaCl, pH 7.2 | 133 | 6 |
| F0569 | Pg (10 mg/mL) Bulk in 10 mM Na Phosphate, 35 mM NaCl, 28.5 mM (0.5%) Arginine, pH 7.2, Filtered (F0199), F/T = 1x | 19 | 1 |

TABLE 9-continued

| Sample ID | Sample Description | Pre-Lyo PMC Count/mL | |
|---|---|---|---|
| | | 10 μm | 25 μm |
| F0570 | Pg (10 mg/mL), 10 mM Sodium Phosphate, 35 mM NaCl, 28.5 mM (0.5%) Arginine, 0.5% CMC, pH 7.2 | 7,783 | 1 |
| F0571 | Pg (10 mg/mL), 10 mM Sodium Phosphate, 35 mM NaCl, 28.5 mM (0.5%) Arginine, 0.1% Phenol, pH 7.2 | 25 | 1 |
| F0572 | Pg (10 mg/mL), 10 mM Sodium Phosphate, 35 mM NaCl, 28.5 mM (0.5%) Arginine, 0.5% Dextran, pH 7.2 | 37 | 1 |

Example 8: Effect of Amino Acid and its Concentration on Plasminogen Aggregation Arginine at 0.5% and 1% were tested in formulations of Plasminogen 10 mg/mL, 35 mM NaCl, 10 mM Sodium Phosphate (NaPi), pH 7.2, after lyophilisation and reconstitution. The particle counts (PMC) are reported in Table 10, which shows that both concentration of arginine are very good to maintain a low PMC value.

TABLE 10

| Assign Sample ID | Sample Description | Reconstitution in dH2O (ml) | Volume (ml) | Pre-Lyo PMC Count/mL | |
|---|---|---|---|---|---|
| | | | | 10 μm | 25 μm |
| F0211 | Pg 10 mg/mL, 28 mM (0.5%) Arg, 35 mM NaCl, 10 mM NaPi, pH 7.2 | 12.5 | 4 | 87 | 2 |
| F0213 | Pg 10 mg/mL, 57 mM (1%) Arg, 35 mM NaCl, 10 mM NaPi, pH 7.2 | 12.5 | 4 | 124 | 11 |

Arginine, glycine and alanine at 1% were compared in formulations of Plasminogen 10 mg/mL, 35 mM NaCl, 10 mM Sodium Phosphate (NaPi), pH 7.2, after lyophilisation and reconstitution. The particle counts (PMC) are reported in Table 11, which shows that arginine is better than alanine and glycine to maintain a low PMC value in the tested conditions, although all these three amino acids provide acceptable PMC values i.e. below 6000 particles equal to or greater than 10 μm per 100 mL.

TABLE 11

| Assign Sample ID | Sample Description | Reconstitution In dH2O (ml) | Volume (ml) | Pre-Lyo PMC_Count/mL | |
|---|---|---|---|---|---|
| | | | | 10 μm | 25 μm |
| F0215 | Pg 10 mg/mL, 57 mM (1%) Arg, 35 mM NaCl, 10 mM NaPi, pH 7.2 | 12.5 | 4 | 178 | 6 |
| F0217 | Pg 10 mg/mL, 57 mM (1%) Gly, 35 mM NaCl, 10 mM NaPi, pH 7.2 | 12.5 | 4 | 881 | 5 |
| F0219 | Pg 10 mg/mL, 57 mM (1%) Ala, 35 mM NaCl, 10 mM NaPi, pH 7.2 | 12.5 | 4 | 5,713 | 9 |

Example 9: Total Percentage of Solid and Osmolality

The osmolality of several formulations of 10 mgl/mL of plasminogen and the percentage of solid matters used to prepare said formulations are reported in Table 12. The osmolality of several formulations of 20 mgl/mL of plasminogen and the percentage of solid matters used to prepare said formulations are reported in Table 13. The resulting osmolality of the tested formulations are advantageously falling within or very close to the physiological range of osmolality. The total percentage of solid matters is calculated from the content of plasminogen, tonicity modifier and bulking agent therein and is a good indicator of the size of the resulting cake after lyophilisation.

TABLE 12

| Assign Sample ID | Sample Description | Total % Solid | mOsm/kg $H_2O$ |
| --- | --- | --- | --- |
| Control | Pg Bulk (10 mg/ml) in 10 mM Na Citrate, 35 mM NaCl, pH 6.5 | 1.0% | 104 |
| F0468 | Pg (10 mg/ml) Bulk in 10 mM Na Citrate, 35 mM NaCl, pH 6.5, 28.5 mM (0.5%) Arginine | 1.5 | 157 |
| F0469 | Pg (10 mg/ml) Bulk in 10 mM Na Citrate, 35 mM NaCl, pH 6.5, 28.5 mM (0.5%) Arginine, 54 mM (1%) Mannitol | 2.5 | 209 |
| F0470 | Pg (10 mg/ml) Bulk in 10 mM Na Citrate, 35 mM NaCl, pH 6.5, 28.5 mM (0.5%) Arginine, 108 mM (2%) Mannitol | 3.5 | 377 |
| F0471 | Pg (10 mg/ml) Bulk in 10 mM Na Citrate, 35 mM NaCl, pH 6.5, 28.5 mM (0.5%) Arginine, 54 mM (1%) Sorbitol | 2.5 | 205 |
| F0472 | Pg (10 mg/ml) Bulk in 10 mM Na Citrate, 35 mM NaCl, pH 6.5, 28.5 mM (0.5%) Arginine, 108 mM (2%) Sorbitol | 3.5 | 298 |
| F0473 | Pg (10 mg/ml) Bulk in 10 mM Na Citrate, 35 mM NaCl, pH 6.5, 57 mM (1%) Arginine | 2.0 | 204 |
| F0474 | Pg (10 mg/ml) Bulk in 10 mM Na Citrate, 35 mM NaCl, pH 6.5, 57 mM (1%) Arginine, 54 mM (1%) Mannitol | 3.0 | 263 |
| F0475 | Pg (10 mg/ml) Bulk in 10 mM Na Citrate, 35 mM NaCl, pH 6.5, 57 mM (1%) Arginine, 108 mM (2%) Mannitol | 4.0 | 325 |
| F0476 | Pg (10 mg/ml) Bulk in 10 mM Na Citrate, 35 mM NaCl, pH 6.5, 57 mM (1%) Arginine, 54 mM (1%) Sorbitol | 3.0 | 252 |
| F0477 | Pg (10 mg/ml) Bulk in 10 mM Na Citrate, 35 mM NaCl, pH 6.5, 57 mM (1%) Arginine, 108 mM (2%) Sorbitol | 4.0 | 294 |
| Control | Pg Bulk (10 mg/ml) in 10 mM Na Phosphate, 35 mM NaCl, pH 7.2 | 1.0% | 106 |
| F0448 | Pg (10 mg/ml) Bulk in 10 mM Na Phosphate, 35 mM NaCl, pH 7.2, 28.5 mM (0.5%) Arginine | 1.5 | 155 |
| F0449 | Pg (10 mg/ml) Bulk in 10 mM Na Phosphate, 35 mM NaCl, pH 7.2, 28.5 mM (0.5%) Arginine, 54 mM (1%) Mannitol | 2.5 | 248 |
| F0450 | Pg (10 mg/ml) Bulk in 10 mM Na Phosphate, 35 mM NaCl, pH 7.2, 28.5 mM (0.5%) Arginine, 108 mM (2%) Mannitol | 3.5 | 345 |
| F0451 | Pg (10 mg/ml) Bulk in 10 mM Na Phosphate, 35 mM NaCl, pH 7.2, 28.5 mM (0.5%) Arginine, 54 mM (1%) Sorbitol | 2.5 | 235 |
| F0452 | Pg (10 mg/ml) Bulk in 10 mM Na Phosphate, 35 mM NaCl, pH 7.2, 28.5 mM (0.5%) Arginine, 108 mM (2%) Sorbitol | 3.5 | 374 |
| F0453 | Pg (10 mg/ml) Bulk in 10 mM Na Phosphate, 35 mM NaCl, pH 7.2, 57 mM (1%) Arginine | 2.0 | 283 |
| F0454 | Pg (10 mg/ml) Bulk in 10 mM Na Phosphate, 35 mM NaCl, pH 7.2, 57 mM (1%) Arginine, 54 mM (1%) Mannitol | 3.0 | 304 |
| F0455 | Pg (10 mg/ml) Bulk in 10 mM Na Phosphate, 35 mM NaCl, pH 7.2, 57 mM (1%) Arginine, 108 mM (2%) Mannitol | 4.0 | 255 |
| F0456 | Pg (10 mg/ml) Bulk in 10 mM Na Phosphate, 35 mM NaCl, pH 7.2, 57 mM (1%) Arginine, 54 mM (1%) Sorbitol | 3.0 | 277 |
| F0457 | Pg (10 mg/ml) Bulk in 10 mM Na Phosphate, 35 mM NaCl, pH 7.2, 57 mM (1%) Arginine, 108 mM (2%) Sorbitol | 4.0 | 284 |
| Control | Pg Bulk (10 mg/ml) in 10 mM Tris-HCl, 35 mM NaCl, pH 8.0 | 1.00% | 86 |
| F0488 | Pg (10 mg/ml) Bulk in 10 mM Tris-HCl, 35 mM NaCl, pH 8.0, 28.5 mM (0.5%) Arginine | 1.5 | 144 |
| F0489 | Pg (10 mg/ml) Bulk in 10 mM Tris-HCl, 35 mM NaCl, pH 8.0, 28.5 mM (0.5%) Arginine, 54 mM (1%) Mannitol | 2.5 | 176 |
| F0490 | Pg (10 mg/ml) Bulk in 10 mM Tris-HCl, 35 mM NaCl, pH 8.0, 28.5 mM (0.5%) Arginine, 108 mM (2%) Mannitol | 3.5 | 324 |
| F0491 | Pg (10 mg/ml) Bulk in 10 mM Tris-HCl, 35 mM NaCl, pH 8.0, 28.5 mM (0.5%) Arginine, 54 mM (1%) Sorbitol | 2.5 | 200 |
| F0492 | Pg (10 mg/ml) Bulk in 10 mM Tris-HCl, 35 mM NaCl, pH 8.0, 28.5 mM (0.5%) Arginine, 108 mM (2%) Sorbitol | 3.5 | 199 |
| F0493 | Pg (10 mg/ml) Bulk in 10 mM Tris-HCl, 35 mM NaCl, pH 8.0, 57 mM (1%) Arginine | 2.0 | 186 |
| F0494 | Pg (10 mg/ml) Bulk in 10 mM Tris-HCl, 35 mM NaCl, pH 8.0, 57 mM (1%) Arginine, 54 mM (1%) Mannitol | 3.0 | 248 |
| F0495 | Pg (10 mg/ml) Bulk in 10 mM Tris-HCl, 35 mM NaCl, pH 8.0, 57 mM (1%) Arginine, 108 mM (2%) Mannitol | 4.0 | 277 |

TABLE 12-continued

| Assign Sample ID | Sample Description | Total % Solid | mOsm/kg H₂O |
|---|---|---|---|
| F0496 | Pg (10 mg/ml) Bulk in 10 mM Tris-HCl, 35 mM NaCl, pH 8.0, 57 mM (1%) Arginine, 54 mM (1%) Sorbitol | 3.0 | 239 |
| F0497 | Pg (10 mg/ml) Bulk P2146 in 10 mM Tris-HCl, 35 mM NaCl, pH 8.0, 57 mM (1%) Arginine, 108 mM (2%) Sorbitol | 4.0 | 290 |

TABLE 13

| Assign Sample ID | Sample Description | Total % Solid | mOsm/kg H₂O |
|---|---|---|---|
| Control | Pg Bulk (20 mg/ml) in 10 mM Na Citrate, 35 mM NaCl, pH 6.5 | 2.0% | 112 |
| F0478 | Pg (20 mg/ml) Bulk in 10 mM Na Citrate, 35 mM NaCl, pH 6.5, 28.5 mM (0.5%) Arginine | 2.5 | 170 |
| F0479 | Pg (20 mg/ml) Bulk in 10 mM Na Citrate, 35 mM NaCl, pH 6.5, 28.5 mM (0.5%) Arginine, 54 mM (1%) Mannitol | 3.5 | 245 |
| F0480 | Pg (20 mg/ml) Bulk in 10 mM Na Citrate, 35 mM NaCl, pH 6.5, 28.5 mM (0.5%) Arginine, 108 mM (2%) Mannitol | 4.5 | 307 |
| F0481 | Pg (20 mg/ml) Bulk in 10 mM Na Citrate, 35 mM NaCl, pH 6.5, 28.5 mM (0.5%) Arginine, 54 mM (1%) Sorbitol | 3.5 | 255 |
| F0482 | Pg (20 mg/ml) Bulk in 10 mM Na Citrate, 35 mM NaCl, pH 6.5, 28.5 mM (0.5%) Arginine, 108 mM (2%) Sorbitol | 4.5 | 306 |
| F0483 | Pg (20 mg/ml) Bulk in 10 mM Na Citrate, 35 mM NaCl, pH 6.5, 57 mM (1%) Arginine | 3.0 | 243 |
| F0484 | Pg (20 mg/ml) Bulk in 10 mM Na Citrate, 35 mM NaCl, pH 6.5, 57 mM (1%) Arginine, 54 mM (1%) Mannitol | 4.0 | 264 |
| F0485 | Pg (20 mg/ml) Bulk in 10 mM Na Citrate, 35 mM NaCl, pH 6.5, 57 mM (1%) Arginine, 108 mM (2%) Mannitol | 5.0 | 341 |
| F0486 | Pg (20 mg/ml) Bulk in 10 mM Na Citrate, 35 mM NaCl, pH 6.5, 57 mM (1%) Arginine, 54 mM (1%) Sorbitol | 4.0 | 337 |
| F0487 | Pg (20 mg/ml) Bulk in 10 mM Na Citrate, 35 mM NaCl, pH 6.5, 57 mM (1%) Arginine, 108 mM (2%) Sorbitol | 5.0 | 370 |
| Control | Pg Bulk P24129 (20 mg/ml) in 10 mM Na Phosphate, 35 mM NaCl, pH 7.2 | 2.0% | 113 |
| F0458 | Pg (20 mg/ml) Bulk in 10 mM Na Phosphate, 35 mM NaCl, pH 7.2, 28.5 mM (0.5%) Arginine | 2.5 | 200 |
| F0459 | Pg (20 mg/ml) Bulk in 10 mM Na Phosphate, 35 mM NaCl, pH 7.2, 28.5 mM (0.5%) Arginine, 54 mM (1%) Mannitol | 3.5 | 265 |
| F0460 | Pg (20 mg/ml) Bulk in 10 mM Na Phosphate, 35 mM NaCl, pH 7.2, 28.5 mM (0.5%) Arginine, 108 mM (2%) Mannitol | 4.5 | 293 |
| F0461 | Pg (20 mg/ml) Bulk in 10 mM Na Phosphate, 35 mM NaCl, pH 7.2, 28.5 mM (0.5%) Arginine, 54 mM (1%) Sorbitol | 3.5 | 279 |
| F0462 | Pg (20 mg/ml) Bulk in 10 mM Na Phosphate, 35 mM NaCl, pH 7.2, 28.5 mM (0.5%) Arginine, 108 mM (2%) Sorbitol | 4.5 | 310 |
| F0463 | Pg (20 mg/ml) Bulk in 10 mM Na Phosphate, 35 mM NaCl, pH 7.2, 57 mM (1%) Arginine | 3.0 | 259 |
| F0464 | Pg (20 mg/ml) Bulk in 10 mM Na Phosphate, 35 mM NaCl, pH 7.2, 57 mM (1%) Arginine, 54 mM (1%) Mannitol | 4.0 | 350 |
| F0465 | Pg (20 mg/ml) Bulk in 10 mM Na Phosphate, 35 mM NaCl, pH 7.2, 57 mM (1%) Arginine, 108 mM (2%) Mannitol | 5.0 | 412 |
| F0466 | Pg (20 mg/ml) Bulk in 10 mM Na Phosphate, 35 mM NaCl, pH 7.2, 57 mM (1%) Arginine, 54 mM (1%) Sorbitol | 4.0 | 366 |
| F0467 | Pg (20 mg/ml) Bulk in 10 mM Na Phosphate, 35 mM NaCl, pH 7.2, 57 mM (1%) Arginine, 108 mM (2%) Sorbitol | 5.0 | 419 |
| Control | Pg Bulk (20 mg/ml) in 10 mM Tris-HCl, 35 mM NaCl, pH 8.0 | 2.0% | 89 |
| F0498 | Pg (20 mg/ml) Bulk in 10 mM Tris-HCl, 35 mM NaCl, pH 8.0, 28.5 mM (0.5%) Arginine | 2.5 | 201 |
| F0499 | Pg (20 mg/ml) Bulk in 10 mM Tris-HCl, 35 mM NaCl, pH 8.0, 28.5 mM (0.5%) Arginine, 54 mM (1%) Mannitol | 3.5 | 260 |
| F0500 | Pg (20 mg/ml) Bulk in 10 mM Tris-HCl, 35 mM NaCl, pH 8.0, 28.5 mM (0.5%) Arginine, 108 mM (2%) Mannitol | 4.5 | 313 |
| F0501 | Pg (20 mg/ml) Bulk in 10 mM Tris-HCl, 35 mM NaCl, pH 8.0, 28.5 mM (0.5%) Arginine, 54 mM (1%) Sorbitol | 3.5 | 200 |
| F0502 | Pg (20 mg/ml) Bulk in 10 mM Tris-HCl, 35 mM NaCl, pH 8.0, 28.5 mM (0.5%) Arginine, 108 mM (2%) Sorbitol | 4.5 | 319 |
| F0503 | Pg (20 mg/ml) Bulk in 10 mM Tris-HCl, 35 mM NaCl, pH 8.0, 57 mM (1%) Arginine | 3.0 | 246 |
| F0504 | Pg (20 mg/ml) Bulk in 10 mM Tris-HCl, 35 mM NaCl, pH 8.0, 57 mM (1%) Arginine, 54 mM (1%) Mannitol | 4.0 | 314 |
| F0505 | Pg (20 mg/ml) Bulk in 10 mM Tris-HCl, 35 mM NaCl, pH 8.0, 57 mM (1%) Arginine, 108 mM (2%) Mannitol | 5.0 | 310 |
| F0506 | Pg (20 mg/ml) Bulk in 10 mM Tris-HCl, 35 mM NaCl, pH 8.0, 57 mM (1%) Arginine, 54 mM (1%) Sorbitol | 4.0 | 282 |

TABLE 13-continued

| Assign Sample ID | Sample Description | Total % Solid | mOsm/kg H₂O |
|---|---|---|---|
| F0507 | Pg (20 mg/ml) Bulk in 10 mM Tris-HCl, 35 mM NaCl, pH 8.0, 57 mM (1%) Arginine, 108 mM (2%) Sorbitol | 5.0 | 279 |

Example 10: Particle Counts (PMC)

The particle counts (PMC) for particles equal or greater than 10 μm of the formulations described in Table 12 are reported in Table 14; and the particle counts (PMC) for particles equal or greater than 10 μm of the formulations described in Table 13 are reported in Table 15.

TABLE 14

| Assign Sample ID | Sample Description | Pre-Lyo PMC Count/mL 10 μm | Lyo-Recon PMC Count/mL 10 μm |
|---|---|---|---|
| Control | Pg Bulk (10 mg/ml) in 10 mM Na Citrate, 35 mM NaCl, pH 6.5 | 379 | 389 |
| F0468 | Pg (10 mg/ml) Bulk in 10 mM Na Citrate, 35 mM NaCl, pH 6.5, 28.5 mM (0.5%) Arginine | 35 | 224 |
| F0469 | Pg (10 mg/ml) Bulk in 10 mM Na Citrate, 35 mM NaCl, pH 6.5, 28.5 mM (0.5%) Arginine, 54 mM (1%) Mannitol | 37 | 136 |
| F0470 | Pg (10 mg/ml) Bulk in 10 mM Na Citrate, 35 mM NaCl, pH 6.5, 28.5 mM (0.5%) Arginine, 108 mM (2%) Mannitol | 33 | 152 |
| F0471 | Pg (10 mg/ml) Bulk in 10 mM Na Citrate, 35 mM NaCl, pH 6.5, 28.5 mM (0.5%) Arginine, 54 mM (1%) Sorbitol | 21 | 159 |
| F0472 | Pg (10 mg/ml) Bulk in 10 mM Na Citrate, 35 mM NaCl, pH 6.5, 28.5 mM (0.5%) Arginine, 108 mM (2%) Sorbitol | 94 | 258 |
| F0473 | Pg (10 mg/ml) Bulk in 10 mM Na Citrate, 35 mM NaCl, pH 6.5, 57 mM (1%) Arginine | 45 | 342 |
| F0474 | Pg (10 mg/ml) Bulk in 10 mM Na Citrate, 35 mM NaCl, pH 6.5, 57 mM (1%) Arginine, 54 mM (1%) Mannitol | 61 | 218 |
| F0475 | Pg (10 mg/ml) Bulk in 10 mM Na Citrate, 35 mM NaCl, pH 6.5, 57 mM (1%) Arginine, 108 mM (2%) Mannitol | 129 | 138 |
| F0476 | Pg (10 mg/ml) Bulk in 10 mM Na Citrate, 35 mM NaCl, pH 6.5, 57 mM (1%) Arginine, 54 mM (1%) Sorbitol | 112 | 401 |
| F0477 | Pg (10 mg/ml) Bulk in 10 mM Na Citrate, 35 mM NaCl, pH 6.5, 57 mM (1%) Arginine, 108 mM (2%) Sorbitol | 155 | 159 |
| Control | Pg Bulk (10 mg/ml) in 10 mM Na Phosphate, 35 mM NaCl, pH 7.2 | 2,400 | 3,819 |
| F0448 | Pg (10 mg/ml) Bulk in 10 mM Na Phosphate, 35 mM NaCl, pH 7.2, 28.5 mM (0.5%) Arginine | 135 | 198 |
| F0449 | Pg (10 mg/ml) Bulk in 10 mM Na Phosphate, 35 mM NaCl, pH 7.2, 28.5 mM (0.5%) Arginine, 54 mM (1%) Mannitol | 171 | 104 |
| F0450 | Pg (10 mg/ml) Bulk in 10 mM Na Phosphate, 35 mM NaCl, pH 7.2, 28.5 mM (0.5%) Arginine, 108 mM (2%) Mannitol | 267 | 254 |
| F0451 | Pg (10 mg/ml) Bulk in 10 mM Na Phosphate, 35 mM NaCl, pH 7.2, 28.5 mM (0.5%) Arginine, 54 mM (1%) Sorbitol | 122 | 133 |
| F0452 | Pg (10 mg/ml) Bulk in 10 mM Na Phosphate, 35 mM NaCl, pH 7.2, 28.5 mM (0.5%) Arginine, 108 mM (2%) Sorbitol | 214 | 176 |
| F0453 | Pg (10 mg/ml) Bulk in 10 mM Na Phosphate, 35 mM NaCl, pH 7.2, 57 mM (1%) Arginine | 37 | 262 |
| F0454 | Pg (10 mg/ml) Bulk in 10 mM Na Phosphate, 35 mM NaCl, pH 7.2, 57 mM (1%) Arginine, 54 mM (1%) Mannitol | 63 | 84 |
| F0455 | Pg (10 mg/ml) Bulk in 10 mM Na Phosphate, 35 mM NaCl, pH 7.2, 57 mM (1%) Arginine, 108 mM (2%) Mannitol | 109 | 150 |
| F0456 | Pg (10 mg/ml) Bulk in 10 mM Na Phosphate, 35 mM NaCl, pH 7.2, 57 mM (1%) Arginine, 54 mM (1%) Sorbitol | 86 | 169 |
| F0457 | Pg (10 mg/ml) Bulk in 10 mM Na Phosphate, 35 mM NaCl, pH 7.2, 57 mM (1%) Arginine, 108 mM (2%) Sorbitol | 85 | 229 |
| Control | Pg Bulk (10 mg/ml) in 10 mM Tris-HCl, 35 mM NaCl, pH 8.0 | 3,341 | 4,007 |
| F0488 | Pg (10 mg/ml) Bulk in 10 mM Tris-HCl, 35 mM NaCl, pH 8.0, 28.5 mM (0.5%) Arginine | 150 | 414 |
| F0489 | Pg (10 mg/ml) Bulk in 10 mM Tris-HCl, 35 mM NaCl, pH 8.0, 28.5 mM (0.5%) Arginine, 54 mM (1%) Mannitol | 151 | 387 |
| F0490 | Pg (10 mg/ml) Bulk in 10 mM Tris-HCl, 35 mM NaCl, pH 8.0, 28.5 mM (0.5%) Arginine, 108 mM (2%) Mannitol | 91 | 528 |
| F0491 | Pg (10 mg/ml) Bulk in 10 mM Tris-HCl, 35 mM NaCl, pH 8.0, 28.5 mM (0.5%) Arginine, 54 mM (1%) Sorbitol | 240 | 589 |
| F0492 | Pg (10 mg/ml) Bulk in 10 mM Tris-HCl, 35 mM NaCl, pH 8.0, 28.5 mM (0.5%) Arginine, 108 mM (2%) Sorbitol | 120 | 507 |

TABLE 14-continued

| Assign Sample ID | Sample Description | Pre-Lyo PMC Count/mL 10 μm | Lyo-Recon PMC Count/mL 10 μm |
|---|---|---|---|
| F0493 | Pg (10 mg/ml) Bulk in 10 mM Tris-HCl, 35 mM NaCl, pH 8.0, 57 mM (1%) Arginine | 103 | 229 |
| F0494 | Pg (10 mg/ml) Bulk in 10 mM Tris-HCl, 35 mM NaCl, pH 8.0, 57 mM (1%) Arginine, 54 mM (1%) Mannitol | 90 | 507 |
| F0495 | Pg (10 mg/ml) Bulk in 10 mM Tris-HCl, 35 mM NaCl, pH 8.0, 57 mM (1%) Arginine, 108 mM (2%) Mannitol | 67 | 256 |
| F0496 | Pg (10 mg/ml) Bulk in 10 mM Tris-HCl, 35 mM NaCl, pH 8.0, 57 mM (1%) Arginine, 54 mM (1%) Sorbitol | 131 | 375 |
| F0497 | Pg (10 mg/ml) Bulk in 10 mM Tris-HCl, 35 mM NaCl, pH 8.0, 57 mM (1%) Arginine, 108 mM (2%) Sorbitol | 62 | 456 |

TABLE 15

| Assign Sample ID | Sample Description | Pre-Lyo PMC Count/mL 10 μm | Lyo-Recon PMC Count/mL 10 μm |
|---|---|---|---|
| Control | Pg Bulk (20 mg/ml) in 10 mM Na Citrate, 35 mM NaCl, pH 6.5 | 1100 | 793 |
| F0478 | Pg (20 mg/ml) Bulk in 10 mM Na Citrate, 35 mM NaCl, pH 6.5, 28.5 mM (0.5%) Arginine | 171 | 358 |
| F0479 | Pg (20 mg/ml) Bulk in 10 mM Na Citrate, 35 mM NaCl, pH 6.5, 28.5 mM (0.5%) Arginine, 54 mM (1%) Mannitol | 118 | 572 |
| F0480 | Pg (20 mg/ml) Bulk in 10 mM Na Citrate, 35 mM NaCl, pH 6.5, 28.5 mM (0.5%) Arginine, 108 mM (2%) Mannitol | 132 | 515 |
| F0481 | Pg (20 mg/ml) Bulk in 10 mM Na Citrate, 35 mM NaCl, pH 6.5, 28.5 mM (0.5%) Arginine, 54 mM (1%) Sorbitol | 96 | 427 |
| F0482 | Pg (20 mg/ml) Bulk in 10 mM Na Citrate, 35 mM NaCl, pH 6.5, 28.5 mM (0.5%) Arginine, 108 mM (2%) Sorbitol | 101 | 585 |
| F0483 | Pg (20 mg/ml) Bulk in 10 mM Na Citrate, 35 mM NaCl, pH 6.5, 57 mM (1%) Arginine | 132 | 286 |
| F0484 | Pg (20 mg/ml) Bulk in 10 mM Na Citrate, 35 mM NaCl, pH 6.5, 57 mM (1%) Arginine, 54 mM (1%) Mannitol | 115 | 537 |
| F0485 | Pg (20 mg/ml) Bulk in 10 mM Na Citrate, 35 mM NaCl, pH 6.5, 57 mM (1%) Arginine, 108 mM (2%) Mannitol | 154 | 362 |
| F0486 | Pg (20 mg/ml) Bulk in 10 mM Na Citrate, 35 mM NaCl, pH 6.5, 57 mM (1%) Arginine, 54 mM (1%) Sorbitol | 114 | 535 |
| F0487 | Pg (20 mg/ml) Bulk in 10 mM Na Citrate, 35 mM NaCl, pH 6.5, 57 mM (1%) Arginine, 108 mM (2%) Sorbitol | 194 | 384 |
| Control | Pg Bulk (20 mg/ml) in 10 mM Na Phosphate, 35 mM NaCl, pH 7.2 | 3,784 | 2,619 |
| F0458 | Pg (20 mg/ml) Bulk in 10 mM Na Phosphate, 35 mM NaCl, pH 7.2, 28.5 mM (0.5%) Arginine | 75 | 398 |
| F0459 | Pg (20 mg/ml) Bulk in 10 mM Na Phosphate, 35 mM NaCl, pH 7.2, 28.5 mM (0.5%) Arginine, 54 mM (1%) Mannitol | 96 | 193 |
| F0460 | Pg (20 mg/ml) Bulk in 10 mM Na Phosphate, 35 mM NaCl, pH 7.2, 28.5 mM (0.5%) Arginine, 108 mM (2%) Mannitol | 128 | 198 |
| F0461 | Pg (20 mg/ml) Bulk in 10 mM Na Phosphate, 35 mM NaCl, pH 7.2, 28.5 mM (0.5%) Arginine, 54 mM (1%) Sorbitol | 123 | 659 |
| F0462 | Pg (20 mg/ml) Bulk in 10 mM Na Phosphate, 35 mM NaCl, pH 7.2, 28.5 mM (0.5%) Arginine, 108 mM (2%) Sorbitol | 103 | 317 |
| F0463 | Pg (20 mg/ml) Bulk in 10 mM Na Phosphate, 35 mM NaCl, pH 7.2, 57 mM (1%) Arginine | 93 | 270 |
| F0464 | Pg (20 mg/ml) Bulk in 10 mM Na Phosphate, 35 mM NaCl, pH 7.2, 57 mM (1%) Arginine, 54 mM (1%) Mannitol | 99 | 386 |
| F0465 | Pg (20 mg/ml) Bulk in 10 mM Na Phosphate, 35 mM NaCl, pH 7.2, 57 mM (1%) Arginine, 108 mM (2%) Mannitol | 139 | 172 |
| F0466 | Pg (20 mg/ml) Bulk in 10 mM Na Phosphate, 35 mM NaCl, pH 7.2, 57 mM (1%) Arginine, 54 mM (1%) Sorbitol | 67 | 681 |
| F0467 | Pg (20 mg/ml) Bulk in 10 mM Na Phosphate, 35 mM NaCl, pH 7.2, 57 mM (1%) Arginine, 108 mM (2%) Sorbitol | 93 | 261 |
| Control | Pg Bulk (20 mg/ml) in 10 mM Tris-HCl, 35 mM NaCl, pH 8.0 | 6,315 | 7,123 |
| F0498 | Pg (20 mg/ml) Bulk in 10 mM Tris-HCl, 35 mM NaCl, pH 8.0, 28.5 mM (0.5%) Arginine | 629 | 3,382 |
| F0499 | Pg (20 mg/ml) Bulk in 10 mM Tris-HCl, 35 mM NaCl, pH 8.0, 28.5 mM (0.5%) Arginine, 54 mM (1%) Mannitol | 1329 | 1,596 |

TABLE 15-continued

| Assign Sample ID | Sample Description | Pre-Lyo PMC Count/mL 10 μm | Lyo-Recon PMC Count/mL 10 μm |
|---|---|---|---|
| F0500 | Pg (20 mg/ml) Bulk in 10 mM Tris-HCl, 35 mM NaCl, pH 8.0, 28.5 mM (0.5%) Arginine, 108 mM (2%) Mannitol | 1007 | 896 |
| F0501 | Pg (20 mg/ml) Bulk in 10 mM Tris-HCl, 35 mM NaCl, pH 8.0, 28.5 mM (0.5%) Arginine, 54 mM (1%) Sorbitol | 649 | 1,401 |
| F0502 | Pg (20 mg/ml) Bulk in 10 mM Tris-HCl, 35 mM NaCl, pH 8.0, 28.5 mM (0.5%) Arginine, 108 mM (2%) Sorbitol | 793 | 684 |
| F0503 | Pg (20 mg/ml) Bulk in 10 mM Tris-HCl, 35 mM NaCl, pH 8.0, 57 mM (1%) Arginine | 459 | 703 |
| F0504 | Pg (20 mg/ml) Bulk in 10 mM Tris-HCl, 35 mM NaCl, pH 8.0, 57 mM (1%) Arginine, 54 mM (1%) Mannitol | 505 | 608 |
| F0505 | Pg (20 mg/ml) Bulk P2147 in 10 mM Tris-HCl, 35 mM NaCl, pH 8.0, 57 mM (1%) Arginine, 108 mM (2%) Mannitol | 155 | 382 |
| F0506 | Pg (20 mg/ml) Bulk in 10 mM Tris-HCl, 35 mM NaCl, pH 8.0, 57 mM (1%) Arginine, 54 mM (1%) Sorbitol | 213 | 898 |
| F0507 | Pg (20 mg/ml) Bulk in 10 mM Tris-HCl, 35 mM NaCl, pH 8.0, 57 mM (1%) Arginine, 108 mM (2%) Sorbitol | 101 | 431 |

Figure 12:
FIG. 12 a picture of vials of lyophilized composition no. F0498 which contains plasminogen 20 mg/ml in 10 mM Tris-HCl, 35 mM NaCl, pH 8.0, and 28.5 mM (0.5%) Arginine.
Figure 13:
FIG. 13 a picture of vials of lyophilized composition no. F0449 which contains plasminogen 10 mg/ml in 10 mM Na Phosphate, 35 mM NaCl, pH 7.2, 28.5 mM (0.5%) Arginine, and 54 mM (1%) Mannitol.
Figure 14:
FIG. 14 a picture of vials of lyophilized composition no. F0459 which contains plasminogen 20 mg/ml in 10 mM Na Phosphate, 35 mM NaCl, pH 7.2, 28.5 mM (0.5%) Arginine, and 54 mM (1%) Mannitol.

Pictures of vials are shown in FIGS. 12, 13 and 14, which contains formulations F0498, F0449 and F0459, respectively, as representative examples of the appearance of the lyophilized formulations reported in Tables 12-15.

Example 10: Reversible Plasminogen Aggregation

Figure 15:
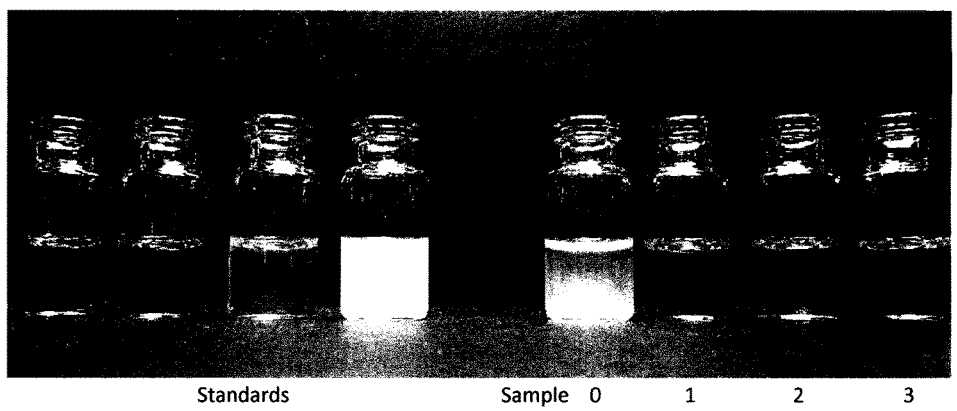
FIG. 15 is a picture of vials containing 5 mg/ml plasminogen in water (Sample 0), in 10 mM sodium citrate buffer pH 6.5 (Sample 1), 10 mM sodium phosphate buffer pH 7.2 (Sample 2) and 10 mM Tris-HCl buffer Ph 8.0 (Sample 3) beside turbidity standards of 0.02, 20, 100, 800 NTU respectively.
Figure 16:
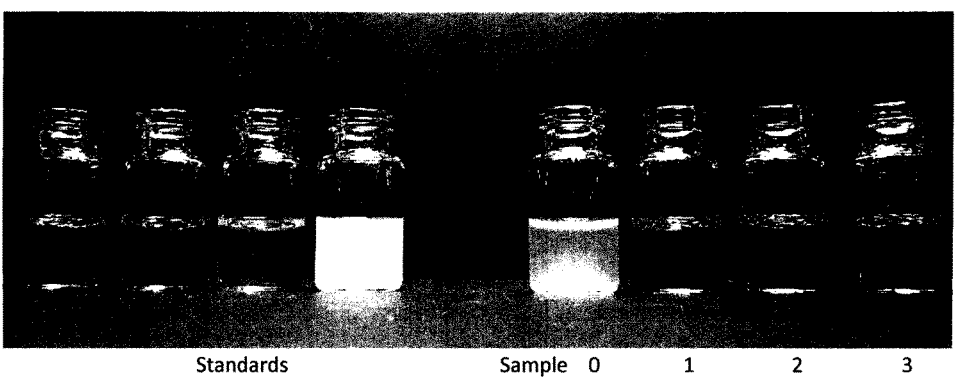
FIG. 16 is a picture of the same vials shown in FIG. 12, with the exception that 35 mM NaCl and 28.5 mM (0.5%) Arg have been added to Samples 1, 2 and 3.

Plasminogen aggregation is reversible as demonstrated by this study. Frozen Plasminogen samples (Pg Bulk) 5 mg/ml, dialyzed in dH2O and heavily precipitated, were thawed, filtered through 1.2 μm syringe filter, and used as starting material for control (Pg control). Aliquots of 2 ml Pg control were added to glass vials, pre-spiked with buffer stocks of 1 M Na Citrate pH 6.5 (Sample 1), 0.5 M Na Phosphate pH 7.2 (Sample 2) or 1 M Tris-HCl pH 8.0 (Sample 3) to obtain final 10 mM buffer concentration at each pH, respectively. Samples 1, 2 and 3 are shown in FIG. 15, where the non-spiked Pg control is Sample 0. Samples 1, 2 and 3 were further spiked with stock solutions of 5 M NaCl and 0.8 M Arginine to obtain a final concentration of 35 mM NaCl and 28.5 mM (0.5%) Arg in each sample and are shown in FIG. 16. Turbidity standards of 0.02, 20, 100, 800 NTU respectively, were used in FIGS. 15 and 16, as reference. It can be noted from FIG. 15 that pH adjustment has dissolved a considerable amount of aggregates. In FIG. 16, the Samples 1, 2 and 3 are rendered transparent by the addition of Arginine and NaCl and no aggregate can be visually detected.

The turbidity of Samples 0, 1, 2 and 3 of FIG. 16 were measured by reading the Optical Density (OD) at 550 nm using standard calibration with turbidity reference standards shown in FIGS. 15 and 16. The turbidity is reported in Nephelometric Turbidity Units (NTU) in Table 16. Aliquots of 1 ml of each sample was measured before (T=0) and after spiking the samples 1, 2 and 3 with buffer, NaCl and Arginine at 0.1 hour, 17 hours, 21 hours and 24 hours. Disaggregation is rapid as it can be noted at only 0.1 hour after spiking, and it is maintained over 24 hours.

TABLE 16

| Assigned Sample ID | Sample Description | Turbidity (NTU by OD 550) | | | | |
|---|---|---|---|---|---|---|
| | | T = 0 | T = 0.1 h | T = 17 h | T = 21 h | T = 24 h |
| F0138 | Pg Bulk (5 mg/ml), Conc. 2x dH2O exchanged | 1008 | 1008 | 1209 | 858 | 372 |
| F0139 | Pg Bulk (5 mg/ml) in 10 mM Sodium Citrate, 35 mM NaCl, 28.5 mM (0.5%) Arginine, pH 6.5 | 1008 | 30 | 37 | 39 | 60 |
| F0140 | Pg Bulk (5 mg/ml) in 10 mM Sodium Phosphate, 35 mM NaCl, 28.5 mM (0.5%) Arginine, pH 7.2 | 1008 | 49 | 60 | 68 | 100 |
| F0141 | Pg Bulk (5 mg/ml) in 10 mM Tris, 35 mM NaCl, 28.5 mM (0.5%) Arginine, pH 8.0 | 1008 | 49 | 56 | 66 | 92 |

Example 11: Effect of Amino Acid Over Time on Composition Turbidity

Figure 18:
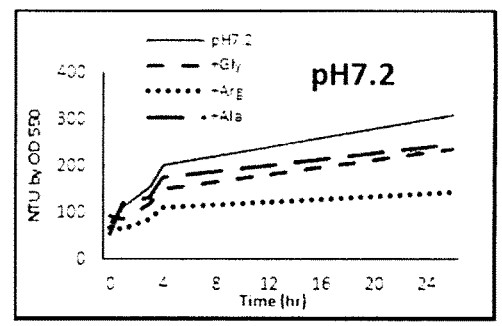
Figure 19:
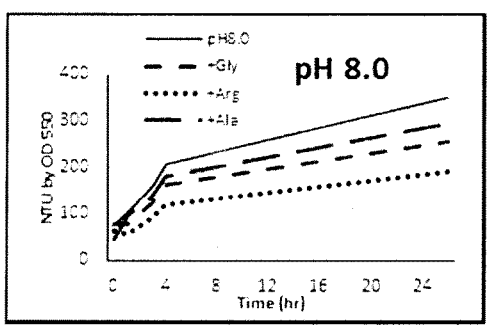

Turbidity has been measured in compositions containing 10 mg plasminogen and 35 mM NaCl with 0.5% glycine, arginine, alanine and without amino acid, at pH 6.5 in sodium citrate buffer (FIG. 17), pH 7.2 in sodium phosphate buffer (FIG. 18), and at pH 8.0 in Tris buffer (FIG. 19).

Figure 17:
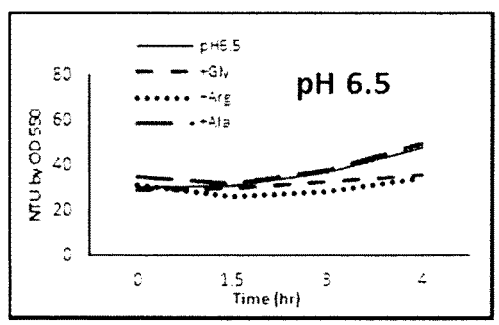
FIGS. 17, 18 and 19 are graphs showing the turbidity over a period of 4 hours for compositions containing 10 mg plasminogen, 35 mM NaCl with 0.5% glycine, arginine, alanine and without amino acid, at pH 6.5 in sodium citrate buffer (FIG. 17), pH 7.2 in sodium phosphate buffer (FIG. 18), and at pH 8.0 in Tris buffer (FIG. 19).
Figure 20:
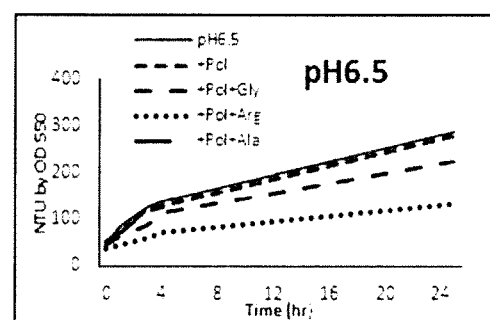
FIGS. 20, 21 and 22 are graphs showing the turbidity over a period of 4 hours for compositions containing 10 mg plasminogen, 35 mM NaCl, 0.5% mannitol with 0.5% glycine, arginine, alanine and without amino acid, at pH 6.5 in sodium citrate buffer (FIG. 20), pH 7.2 in sodium phosphate buffer (FIG. 21), and at pH 8.0 in Tris buffer (FIG. 22).
Figure 21:
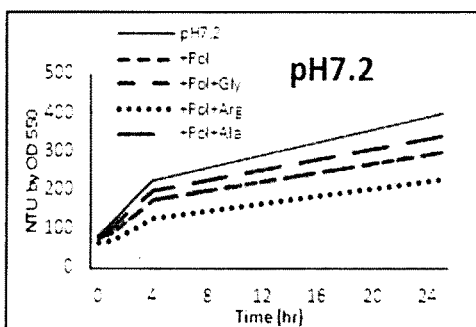
Figure 22:
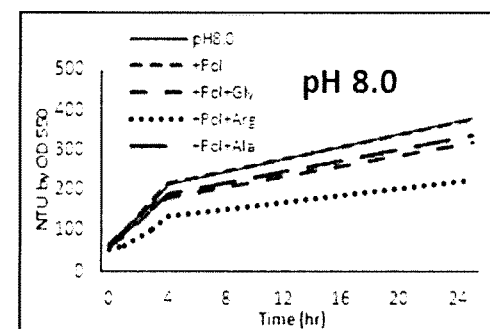

The compositions tested in FIGS. 17, 18 and 19 were reproduced in presence of 0.5% mannitol as a bulking agent, and reported in FIGS. 20, 21 and 22, respectively.

In all cases, the presence of the amino acid provides a stabilizing effect and maintain or lower the turbidity. Comparing the type of amino acids, arginine shows the best stabilizing effect and lower the turbidity at all tested pH and in presence and absence of bulking agent, i.e. 0.5% mannitol.

Example 12: Composition of Elevated Concentration of Plasminogen

Compositions containing a high concentration of plasminogen have been studied. The PMC counts for particles of 10 μm or greater, and of 25 μm or greater have been reported in Table 17 for compositions of 20 mg/ml plasminogen in 10 mM or 100 mM sodium citrate, 35 mM NaCl, at pH6.5, with and without 1% arginine, and compositions of 37 and 56 mg/ml plasminogen in 100 mM sodium citrate, 35 mM NaCl, at pH6.5, with 1% arginine.

Table 17 shows that the formulations of the present invention advantageously allow the preparation of compositions comprising elevated concentrations of plasminogen (37 and 56 mg/ml) without causing inacceptable level of particles.

TABLE 17

| Assign Sample | | PMC_Count/Vial | |
|---|---|---|---|
| ID | Sample Description | 10 μm | 25 μm |
| P24138 | Pg (20 mg/ml) Bulk in 10 mM Na Citrate, 35 mM NaCl, pH 6.5 | 983 | 8 |
| F0483 | Pg (20 mg/ml) Bulk in 10 mM Na Citrate, 35 mM NaCl, pH 6.5, 57 mM (1%) Arginine | 525 | 0 |
| F0614 | Pg (20 mg/ml) Bulk in 10 mM Na Citrate, 100 mM NaCl, pH 6.5, 57 mM (1%) Arginine | 667 | 33 |
| F0615 | Pg (37 mg/ml) Bulk in 10 mM Na Citrate, 100 mM NaCl, pH 6.5, 57 mM (1%) Arginine | 325 | 33 |
| F0616 | Pg (56 mg/ml) Bulk in 10 mM Na Citrate, 100 mM NaCl, pH 6.5, 57 mM (1%) Arginine | 292 | 17 |

Example 13: Plasminogen Activity

The plasminogen activity for each formulation exemplified herein was tested and compared to the plasminogen activity of the initial preparation or bulk preparation (Pg bulk). It has been noted that the plasminogen activity is not affected by any of these formulations.

The invention claimed is:

1. A pharmaceutical composition comprising:
   plasminogen, in a concentration from 0.01 mg/ml to 80 mg/ml;
   a tonicity modifier, which contains sodium, wherein the tonicity modifier is in a concentration adjusted to reach an osmolality of the composition between 180 mOsm and 350 mOsm; and
   a stabilizing agent, which is arginine or glycine, in a concentration from 20 mM to 200 mM;
   wherein the composition has a pH of 3.0 to 10.0, and
   wherein (a) the plasminogen represents at least 80% of the total protein content of the composition;
   (b) the composition further comprises a non-reducing sugar, which is sucrose;
   (c) the plasminogen is constituted of more than 80% of Glu-plasminogen; or
   (d) the composition contains an amount of particles equal to or greater than 10 μm that is lower than 6000 particles per container, when the container has a nominal content of less than or equal to 100 ml.

2. The pharmaceutical composition of claim 1, wherein the pH is from 5.0 to 8.0.

3. The pharmaceutical composition of claim 1, wherein the concentration of plasminogen is from 5 mg/ml to 60 mg/ml.

4. The pharmaceutical composition of claim 1, wherein plasminogen represents at least 80% of the total protein content of the composition.

5. The pharmaceutical composition of claim 1, wherein the stabilising agent is arginine.

6. The pharmaceutical composition of claim 1, wherein the stabilising agent is glycine.

7. The pharmaceutical composition of claim 1, wherein the stabilising agent is in a concentration of 25 mM to 75 mM.

8. The pharmaceutical composition of claim 1, wherein the tonicity modifier is sodium chloride.

9. The pharmaceutical composition of claim 1, wherein the tonicity modifier is present in a concentration of 30 mM to 250 mM.

10. The pharmaceutical composition of claim 1, wherein the tonicity modifier is present in a concentration of from 30 mM to 100 mM.

11. The pharmaceutical composition of claim 1, further comprising a non-reducing sugar, which is sucrose.

12. The pharmaceutical composition of claim 1, wherein the composition is substantially free of aprotinin.

13. The pharmaceutical composition of claim 1, wherein said plasminogen is constituted of more than 80% of Glu-plasminogen.

14. The pharmaceutical composition of claim 1, wherein said plasminogen is Glu-plasminogen.

15. The pharmaceutical composition of claim 1, wherein the composition contains an amount of particles equal to or greater than 10 μm that is lower than 6000 particles per container, when the container has a nominal content of less than or equal to 100 ml.

16. The pharmaceutical composition of claim 1, which is suitable for intravenous, subcutaneous, topical, intradermal, ophthalmic and/or intramuscular administration.

17. The pharmaceutical composition of claim 1, which is a liquid composition, a liquid composition suitable for lyophilisation, a liquid composition suitable for freezing, a lyophilised composition, a frozen composition or a reconstituted composition.

18. A pharmaceutical composition comprising plasminogen, which contains an amount of particles equal to or greater than 10 μm that is lower than 6000 particles per container, when the container has a nominal content of less than or equal to 100 ml, which comprises a stabilising agent that is arginine or glycine.

19. The pharmaceutical composition of claim 18, wherein the stabilising agent is arginine.

20. The pharmaceutical composition of claim 18, wherein the stabilising agent is glycine.

21. The pharmaceutical composition of claim 18, wherein the stabilising agent is in a concentration from 20 mM to 200 mM.

22. The pharmaceutical composition of claim 18, further comprising a non-reducing sugar, which is sucrose.

23. The pharmaceutical composition of claim 18, wherein the concentration of plasminogen is from 0.01 mg/ml to 80 mg/ml.

24. The pharmaceutical composition of claim 18, wherein plasminogen represents more than 95% of the total protein content of the composition.

25. The pharmaceutical composition of claim 18, which further comprises a tonicity modifier, which contains sodium.

26. The pharmaceutical composition of claim 25, wherein the tonicity modifier is sodium chloride.

27. The pharmaceutical composition of claim 25, wherein the tonicity modifier is in a concentration adjusted to reach an osmolality of the pharmaceutical composition between 180 mOsm and 350 mOsm.

28. The pharmaceutical composition of claim 25, wherein the tonicity modifier is present in a concentration of 30 mM to 250 mM.

29. The pharmaceutical composition of claim 18, wherein the pharmaceutical composition has an osmolality between 180 mOsm and 350 mOsm.

30. The pharmaceutical composition of claim 18, wherein the pharmaceutical composition has a pH of 5.0 to 8.0.

31. The pharmaceutical composition of claim 18, wherein the composition is substantially free of aprotinin.

32. The pharmaceutical composition of claim 18, wherein said plasminogen consists of more than 80% of Glu-plasminogen.

33. The pharmaceutical composition of claim 18, wherein said plasminogen is Glu-plasminogen.

34. The pharmaceutical composition of claim 18, which is suitable for intravenous, subcutaneous, topical, intradermal, ophthalmic and/or intramuscular administration.

35. The pharmaceutical composition of claim 18, which is a liquid composition, a liquid composition suitable for lyophilisation, a liquid composition suitable for freezing, a lyophilised composition, a frozen composition or a reconstituted composition.

36. A pharmaceutical composition having a pH of 6.0 to 8.0 comprising:
   i) from 2 mg/ml to 20 mg/ml of Glu-plasminogen;
   ii) from 30 mM to 100 mM of sodium chloride;
   iii) from 10 mM to 100 mM of glycine;
   iv) from 50 mM to 150 mM of sucrose; and
   v) from 2 mM to 30 mM of a citrate buffer.

37. The pharmaceutical composition of claim 36, wherein said composition has a pH of 6.0 to 7.0 and comprises:
   i) from 5 mg/ml to 20 mg/ml of Glu-plasminogen;
   ii) from 35 mM to 75 mM of sodium chloride;
   iii) from 25 mM to 75 mM of glycine;
   iv) from 54 mM to 108 mM of sucrose; and
   v) 10 mM of sodium citrate buffer.

38. The pharmaceutical composition of claim 1, wherein the composition comprises any combination of at least two of (a)-(d).

* * * * *